US012342082B2

(12) United States Patent
Nishide et al.

(10) Patent No.: US 12,342,082 B2
(45) Date of Patent: Jun. 24, 2025

(54) PROGRAM, INFORMATION PROCESSING METHOD, AND ENDOSCOPE SYSTEM FOR GENERATING A COMPOSITE ENDOSCOPIC IMAGE

(71) Applicant: HOYA CORPORATION, Tokyo (JP)

(72) Inventors: Akihiko Nishide, Tokyo (JP); Junko Sugai, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 282 days.

(21) Appl. No.: 18/019,911

(22) PCT Filed: Sep. 6, 2021

(86) PCT No.: PCT/JP2021/032584
§ 371 (c)(1),
(2) Date: Feb. 6, 2023

(87) PCT Pub. No.: WO2022/070782
PCT Pub. Date: Apr. 7, 2022

(65) Prior Publication Data
US 2023/0353879 A1 Nov. 2, 2023

(30) Foreign Application Priority Data
Oct. 2, 2020 (JP) ................................ 2020-167752

(51) Int. Cl.
*H04N 23/698* (2023.01)
*G06T 5/50* (2006.01)
(Continued)

(52) U.S. Cl.
CPC ............. *H04N 23/698* (2023.01); *G06T 5/50* (2013.01); *G06T 5/80* (2024.01); *H04N 13/106* (2018.05)

(58) Field of Classification Search
CPC ...... H04N 23/698; H04N 13/106; G06T 5/80; G06T 5/50; A61B 1/0676
See application file for complete search history.

(56) References Cited

U.S. PATENT DOCUMENTS

| 8,758,263 | B1 * | 6/2014 | Rahimian | ............ A61B 90/13 |
| | | | | 600/417 |
| 11,627,871 | B2 * | 4/2023 | Weber | ............ A61B 1/0646 |
| | | | | 600/178 |

(Continued)

FOREIGN PATENT DOCUMENTS

| JP | H09-80319 A | 3/1997 |
| JP | 2009-22411 A | 2/2009 |

(Continued)

OTHER PUBLICATIONS

Supplementary European Search Report issued in European Patent Office application No. 21875084.2, dated Jul. 5, 2024.

(Continued)

*Primary Examiner* — Mohamed A. Wasel
(74) *Attorney, Agent, or Firm* — GREENBLUM & BERNSTEIN, P.L.C.

(57) ABSTRACT

A program causes a computer to execute processing including acquiring endoscopic images obtained by capturing images of a subject by a plurality of imaging units arranged on an end surface and a peripheral surface of a tubular distal end portion provided in an insertion portion of an endoscope, generating a composite image obtained by combining a plurality of the captured endoscopic images so as to form a view of an entire circumferential direction including a front visual field and a rear visual field with respect to the distal end portion, acquiring an insertion distance and a rotation angle of the endoscope inserted into a body of the subject at a time point when the endoscopic images are (Continued)

captured, and outputting the composite image in association with the acquired insertion distance and rotation angle of the endoscope.

12 Claims, 19 Drawing Sheets

(51) Int. Cl.
*G06T 5/80* (2024.01)
*H04N 13/106* (2018.01)

(56) References Cited

U.S. PATENT DOCUMENTS

| | | | |
|---|---|---|---|
| 2013/0296649 A1 | 11/2013 | Kirma et al. | |
| 2014/0288366 A1* | 9/2014 | Ohkoba | A61B 1/00087 600/104 |
| 2015/0313445 A1 | 11/2015 | Davidson et al. | |
| 2016/0103312 A1 | 4/2016 | Furuta | |
| 2017/0257619 A1 | 9/2017 | Kashima | |
| 2017/0325669 A1 | 11/2017 | Levy | |
| 2017/0333125 A1 | 11/2017 | Lepak et al. | |
| 2018/0368658 A1* | 12/2018 | Yamamoto | A61B 1/00163 |
| 2019/0388175 A1 | 12/2019 | Tatsuta et al. | |
| 2020/0281449 A1* | 9/2020 | Yoshimura | A61B 90/361 |
| 2021/0398274 A1 | 12/2021 | Nishide | |
| 2022/0198742 A1* | 6/2022 | Nishide | G06V 10/82 |
| 2022/0293268 A1 | 9/2022 | Nishide | |
| 2022/0327707 A1 | 10/2022 | Nishide | |
| 2022/0351407 A1 | 11/2022 | Nishide et al. | |
| 2022/0409029 A1 | 12/2022 | Nishide et al. | |

FOREIGN PATENT DOCUMENTS

| | | |
|---|---|---|
| JP | 2010-279539 A | 12/2010 |
| JP | 2011-172692 A | 9/2011 |
| JP | 2013-431 | 1/2013 |
| JP | 2013-542467 A | 11/2013 |
| JP | 2015-16021 A | 1/2015 |
| JP | 2016-180998 A | 10/2016 |
| JP | 2018-519860 A | 7/2018 |
| JP | 2018-151540 A | 9/2018 |
| JP | 2018-535739 A | 12/2018 |
| JP | 2019-138755 A | 8/2019 |
| WO | 2016/043063 A1 | 3/2016 |
| WO | 2018/180249 A1 | 4/2018 |

OTHER PUBLICATIONS

U.S. Appl. No. 17/786,321 to Akihiko Nishide et al., filed Jun. 16, 2022.

International Search Report issued in International Bureau of WIPO Patent Application No. PCT/JP2021/032584, dated Oct. 26, 2021, along with an English translation thereof.

* cited by examiner

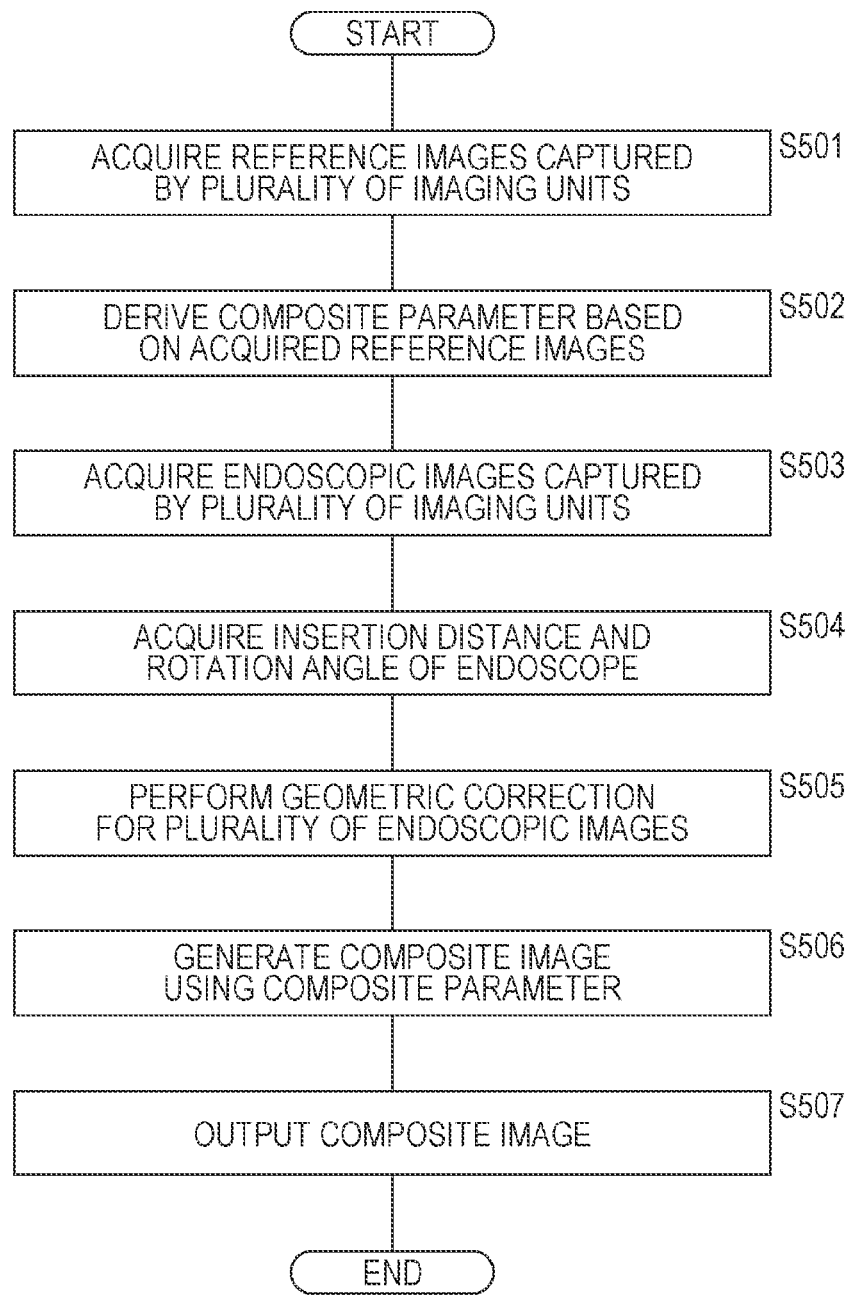

PROGRAM, INFORMATION PROCESSING METHOD, AND ENDOSCOPE SYSTEM FOR GENERATING A COMPOSITE ENDOSCOPIC IMAGE

TECHNICAL FIELD

The present technology relates to a program, an information processing method, and an endoscope system. The present application claims priority based on Japanese Patent Application No, 2020-167752 filed on Oct. 2, 2020, the entire contents of which are incorporated herein by reference.

BACKGROUND ART

An endoscope is a medical instrument to be inserted into a body cavity of a subject to observe and treat a desired site, and includes an imaging unit provided in a distal end portion of an insertion tube to be inserted into the body cavity, and an illumination device illuminating an imaging field of view of the imaging unit. Patent Literature 1 discloses an endoscope including an illumination device for achieving illumination in a wide angular range of 180 degrees or more to enable observation at a wide viewing angle.

CITATION LIST

Patent Literature

Patent Literature 1: JP 2015-16021 A

SUMMARY OF INVENTION

Technical Problem

However, the endoscope device described in Literature 1 has a problem that it is not considered to generate an image configured on the basis of captured images captured by a plurality of imaging units. In addition, there is also a problem that there is no method of displaying the captured images captured by the plurality of imaging units on a plurality of display devices. In addition, there is also a problem that a display method such as development view display of a virtual endoscopic image of the X-ray CT does not exist in the endoscope device.

In one aspect, an object is to provide a program or the like capable of generating an image configured on the basis of captured images captured by a plurality of imaging units. It is also aimed to display the virtual endoscopic image of the X-ray CT by the same development view display method as the development view display of the virtual endoscopic image of the X-ray CT, and to facilitate correspondence with the virtual endoscopic image of the X-ray CT.

Solution to Problem

A program according to one aspect of the present disclosure causes a computer to execute processing including acquiring endoscopic images obtained by capturing images of a subject by a plurality of imaging units arranged on an end surface and a peripheral surface of a tubular distal end portion provided in an insertion portion of an endoscope, generating a composite image obtained by combining a plurality of the captured endoscopic images so as to form a view of an entire circumferential direction including a front visual field and a rear visual field with respect to the distal end portion, acquiring an insertion distance and a rotation angle of the endoscope inserted into a body of the subject at a time point when the endoscopic images are captured, and outputting the composite image in association with the acquired insertion distance and rotation angle of the endoscope.

An information processing method according to one aspect of the present causes a computer to execute processing including acquiring endoscopic images obtained by capturing images of a subject by a plurality of imaging units arranged on an end surface and a peripheral surface of a tubular distal end portion provided in an insertion portion of an endoscope, generating a composite image obtained by combining a plurality of the captured endoscopic images so as to form a view of an entire circumferential direction including a front visual field and a rear visual field with respect to the distal end portion, acquiring an insertion distance and a rotation angle of the endoscope inserted into a body of the subject at a time point when the endoscopic images are captured, and outputting the composite image in association with the acquired insertion distance and rotation angle of the endoscope.

A program according to one aspect of the present disclosure causes a computer to execute processing including acquiring endoscopic images obtained by capturing images of a subject by a plurality of imaging units arranged at a distal end portion provided in an insertion portion of an endoscope, generating a composite image obtained by combining a plurality of the captured endoscopic images so as to form a view of an entire and a rear visual field with respect to the distal end portion, and outputting the generated composite image, in which the processing of generating the composite image includes acquiring reference images obtained by capturing images of a predetermined reference object by a plurality of the imaging units, deriving an image composite parameter based on the acquired reference images, and generating the composite image using the derived image composite parameter. The program may cause the computer to execute processing including processing of generating an endoscopic development view corresponding to a development view display of an endoscopic image by a virtual endoscopic image of X-ray CT and comparing the development view display of the endoscope with the development view display of X-ray CT.

An information processing method according to one aspect of the present causes a computer to execute processing including acquiring endoscopic images obtained by capturing images of a subject by a plurality of imaging units arranged at a distal end portion provided in an insertion portion of an endoscope, generating a composite image obtained by combining a plurality of the captured endoscopic images so as to form a view of an entire and a rear visual field with respect to the distal end portion, and outputting the generated composite image, in which the processing of generating the composite image includes acquiring reference images obtained by capturing images of a predetermined reference object by a plurality of the imaging units, deriving an image composite parameter based on the acquired reference images, and generating the composite image using the derived image composite parameter. The information processing method may cause the computer to execute processing including processing of generating an endoscopic development view corresponding to a development view display of an endoscopic image by a virtual endoscopic image of X-ray CT and comparing the development view display of the endoscope with the development view display of X-ray CT.

An endoscope system according to one aspect of the present includes an endoscope and a control unit that processes an endoscopic image captured by the endoscope and is an endoscope comprising an insertion portion to be inserted in a body of a subject, and a plurality of imaging units provided to a tubular distal end portion at a tip of the insertion portion, in which the plurality of imaging units capture a plurality of endoscopic images including a front visual field and a rear visual field in an entire circumferential direction with respect to the distal end portion, and the control unit acquires endoscopic images obtained by capturing images of the subject by the plurality of imaging units, combines the plurality of the endoscopic images captured at a plurality of time points to generate a composite image including the rear visual field with respect to the distal end portion, and outputs the generated composite image. The endoscope system may generate an endoscopic development view corresponding to a development view display of an endoscopic image by a virtual endoscopic image of X-ray CT and output information to compare the development view display of the endoscope with the development view display of X-ray CT.

Advantageous Effects of Invention

According to the present disclosure, a program or the like is provided that is capable of generating an image configured on the basis of captured images captured by a plurality of imaging units.

BRIEF DESCRIPTION OF DRAWINGS

FIG. 22 is a flowchart illustrating an example of a processing procedure in the control unit.

DESCRIPTION OF EMBODIMENTS

First Embodiment

Figure 1:
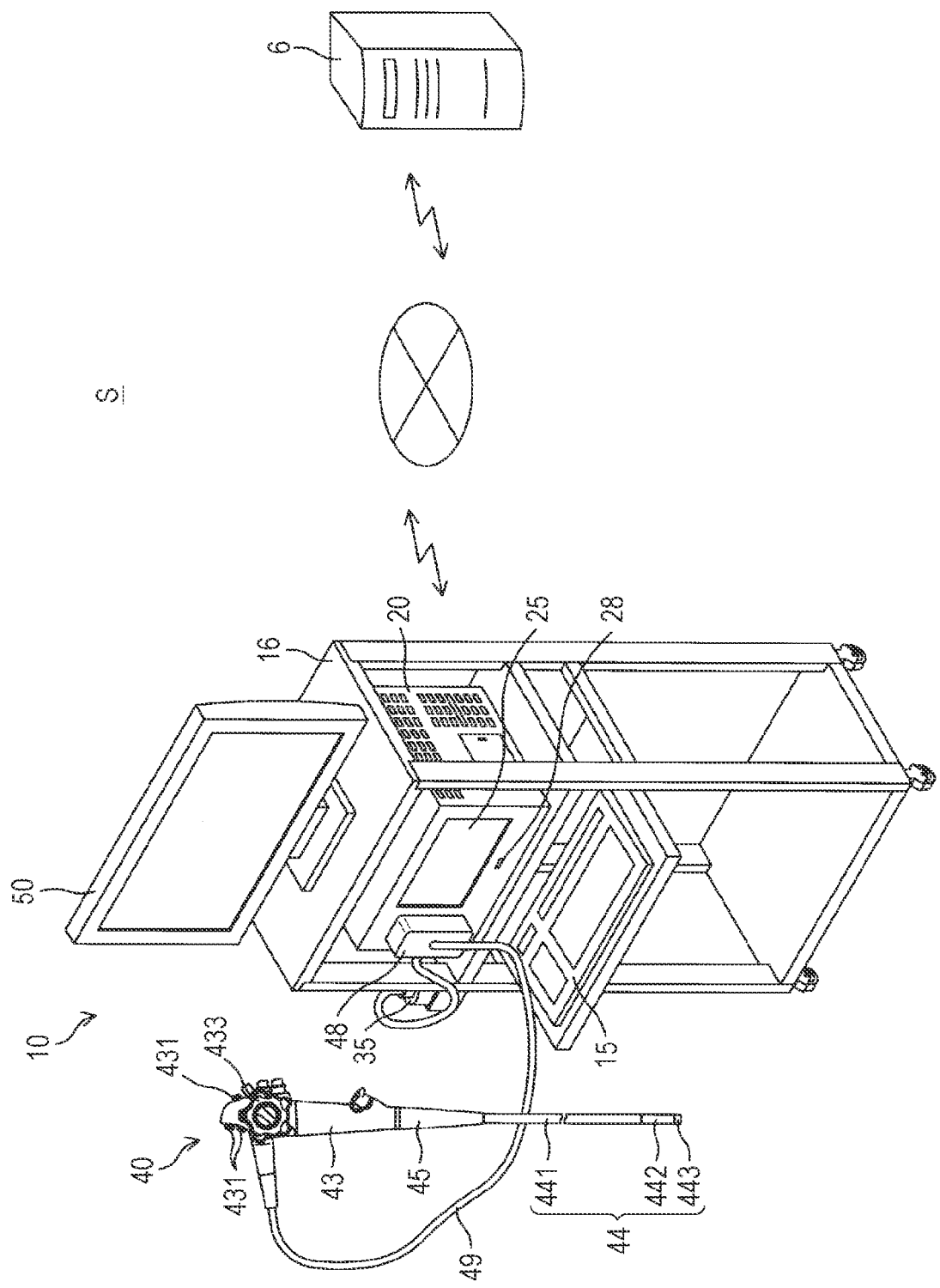
FIG. 1 is a schematic diagram illustrating an outline of an endoscope system according to a first embodiment (endoscopic development view).

Hereinafter, the present invention will be described in detail with reference to the drawings illustrating embodiments of the present invention. FIG. 1 is a schematic diagram illustrating an outline of a diagnosis support system according to a first embodiment (endoscopic development view). An endoscope system S includes an endoscope device 10 and an information processing device 6 communicably connected to the endoscope device 10.

The endoscope device 10 transmits images (captured images) captured by imaging units 446 of an endoscope 40 to a processor 20 for an endoscope, and the processor 20 for an endoscope performs various types of image processing such as gamma correction, white balance correction, and shading correction, thereby generating endoscopic images set to be easily observed by an operator. The endoscope device 10 outputs (transmits) the generated endoscopic images to the information processing device 6. In a case where the information processing device 6 acquires the endoscopic image transmitted from the endoscope device 10, the information processing device 6 performs various types of information processing based on these endoscopic images and outputs information on diagnosis assistance.

The endoscope device 10 includes the processor 20 for an endoscope, the endoscope 40, and a display device 50. The display device 50 is, for example, a liquid crystal display device or an organic electro luminescence (EL) display device.

The display device 50 is provided on an upper shelf of a storage rack 16 with casters. The processor 20 for an endoscope is stored in a middle shelf of the storage rack 16. The storage rack 16 is arranged in the vicinity of a bed for an endoscopic examination (not illustrated). The storage rack 16 includes a pull-out shelf on which a keyboard 15 connected to the processor 20 for an endoscope is provided.

The processor 20 for an endoscope has a substantially rectangular parallelepiped shape and is provided with a touch panel 25 on one surface. Below the touch panel 25, a reading unit 28 is arranged. The reading unit 28 is a connection interface for performing reading and writing on a portable recording medium such as a USB connector, a secure digital (SD) card slot, a compact disc read only memory (CD-ROM) drive, or the like.

The endoscope 40 includes an insertion portion 44, an operation unit 43, a universal cord 49, and a scope connector 48. The operation unit 43 is provided with a control button 431. The insertion portion 44 is long and has one end connected to the operation unit 43 via a bend preventing portion 45. The insertion portion 44 includes a soft portion 441, a bending section 442, and a distal end portion 443 in order from a side of the operation unit 43. The bending section 442 is bent according to an operation of a bending knob 433. Physical detection devices such as a three-axis acceleration sensor, a gyro sensor, a geomagnetic sensor, a magnetic coil sensor, and an endoscope-insertion-type observation device (colonoscope navigation) may be installed in the insertion portion 44. In a case where the endoscope 40 is inserted into a body of a subject, detection results from these physical detection devices may be acquired.

The universal cord 49 is long and has a first end connected to the operation unit 43 and a second end connected to the scope connector 48. The universal cord 49 is soft. The scope connector 48 has a substantially rectangular parallelepiped shape. The scope connector 48 is provided with an air/water supply port 36 (see FIG. 2) for connecting an air/water supply tube.

Figure 2:
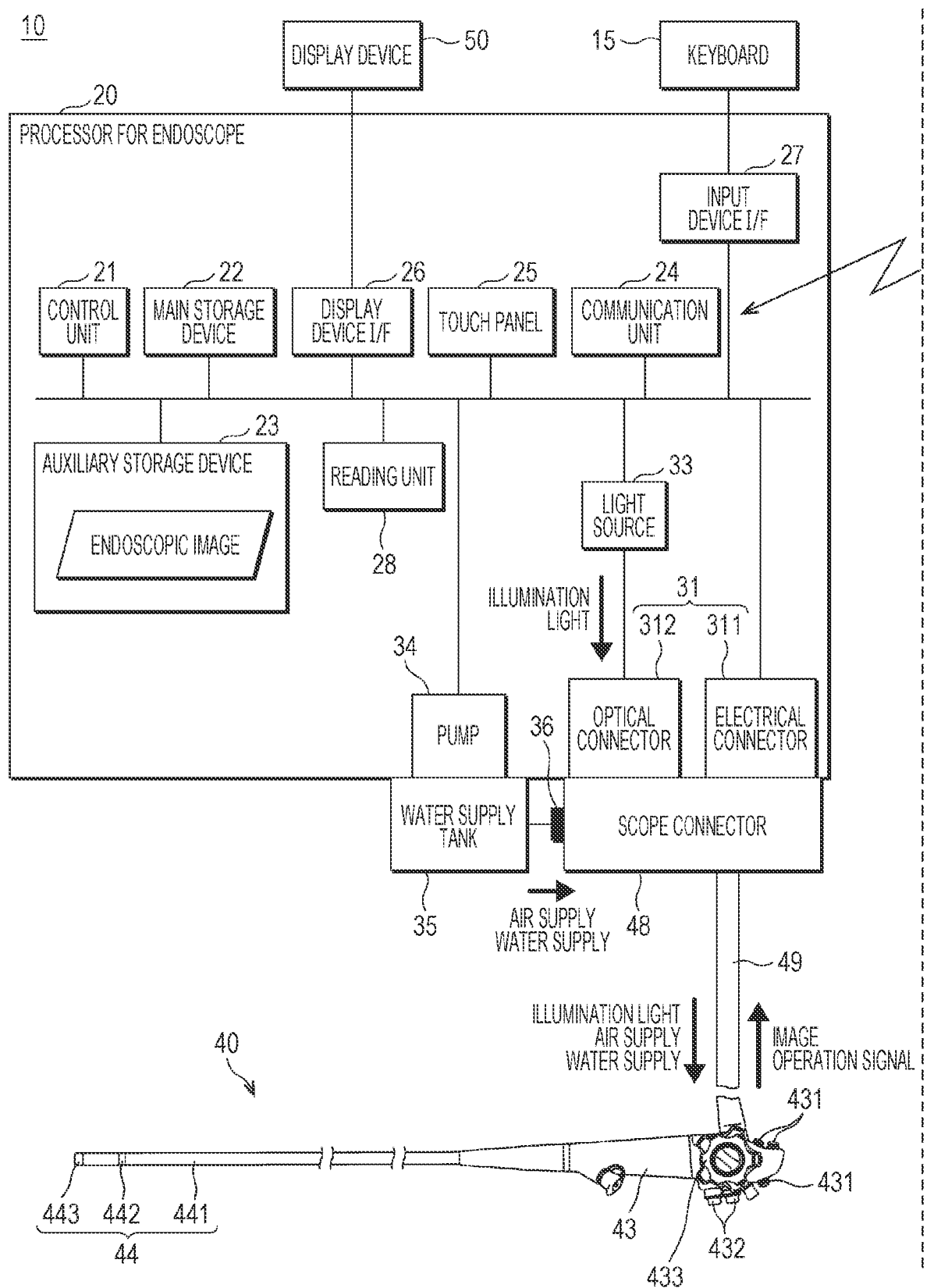
FIG. 2 is a block diagram illustrating a configuration example of the endoscope device included in an endoscope system.

FIG. 2 is a block diagram illustrating a configuration example of the endoscope device included in the endoscope system. The control unit 21 is an arithmetic control device that executes a program (program product) according to the present embodiment. One or a plurality of central processing units (CPUs), graphics processing units (GPUs), multi-core CPUs, or the like is used for the control unit 21. The control unit 21 is connected to each hardware unit constituting the processor 20 for an endoscope via the bus.

A main storage device 22 is, for example, a storage device such as a static random access memory (SRAM), a dynamic random access memory (DRAM), or a flash memory. The main storage device 22 temporarily stores information necessary in processing performed by the control unit 21 and a program (program product) being executed by the control unit 21. An auxiliary storage device 23 is, for example, a storage device such as an SRAM, a flash memory, or a hard disk and is a storage device having a capacity larger than that of the main storage device 22. In the auxiliary storage device 23, for example, the acquired captured image and the generated endoscopic image may be stored as intermediate data.

A communication unit 24 is a communication module or a communication interface for performing communication with the information processing device 6 via a network in a wired or wireless manner and is, for example, a narrow-area wireless communication module such as Wi-Fi (registered trademark) or Bluetooth (registered trademark) or a wide-area wireless communication module such as 4G or Long Term Evolution (LTE). The touch panel 25 includes a display unit such as a liquid crystal display panel and an input unit layered on the display unit.

A display device I/F 26 is an interface for connecting the processor 20 for an endoscope and the display device 50 to each other. An input device I/F 27 is an interface for connecting the processor 20 for an endoscope and an input device such as the keyboard 15 to each other.

A light source 33 is a high-luminance white light source such as a white LED or a xenon lamp. The light source 33 is connected to the bus via a driver (not illustrated). In the light source 33, turning on, turning off, and a change of luminance are controlled by the control unit 21. Illumination light emitted from the light source 33 is incident on an optical connector 312. The optical connector 312 engages with the scope connector 48 to supply the illumination light to the endoscope 40.

A pump 34 generates a pressure for the air supply and water supply function of the endoscope 40. The pump 34 is connected to the bus via a driver (not illustrated). In the pump 34, turning on, turning off, and a change of the pressure are controlled by the control unit 21. The pump 34 is connected to the air/water supply port 36 provided in the scope connector 48 via a water supply tank 35.

An outline of functions of the endoscope 40 connected to the processor 20 for an endoscope will be described. A fiber bundle, a cable bundle, an air supply tube, a water supply tube, and the like are inserted inside the scope connector 48, the universal cord 49, the operation unit 43, and the insertion portion 44. The illumination light emitted from the light source 33 is emitted from an illumination window provided at the distal end portion 443 via the optical connector 312 and the fiber bundle. The imaging unit provided at the distal end portion 443 captures an image of a range illuminated by the illumination light. The captured image is transmitted from the imaging unit to the processor 20 for an endoscope via the cable bundle and an electrical connector 311.

The control unit 21 of the processor 20 for an endoscope functions as an image processing unit 211 by executing a program stored in the main storage device 22. The image processing unit 211 performs various types of image processing such as gamma correction, white balance correction, and shading correction on the image (captured image) output from the endoscope 40 and outputs the image as an endoscopic image.

Figure 3:
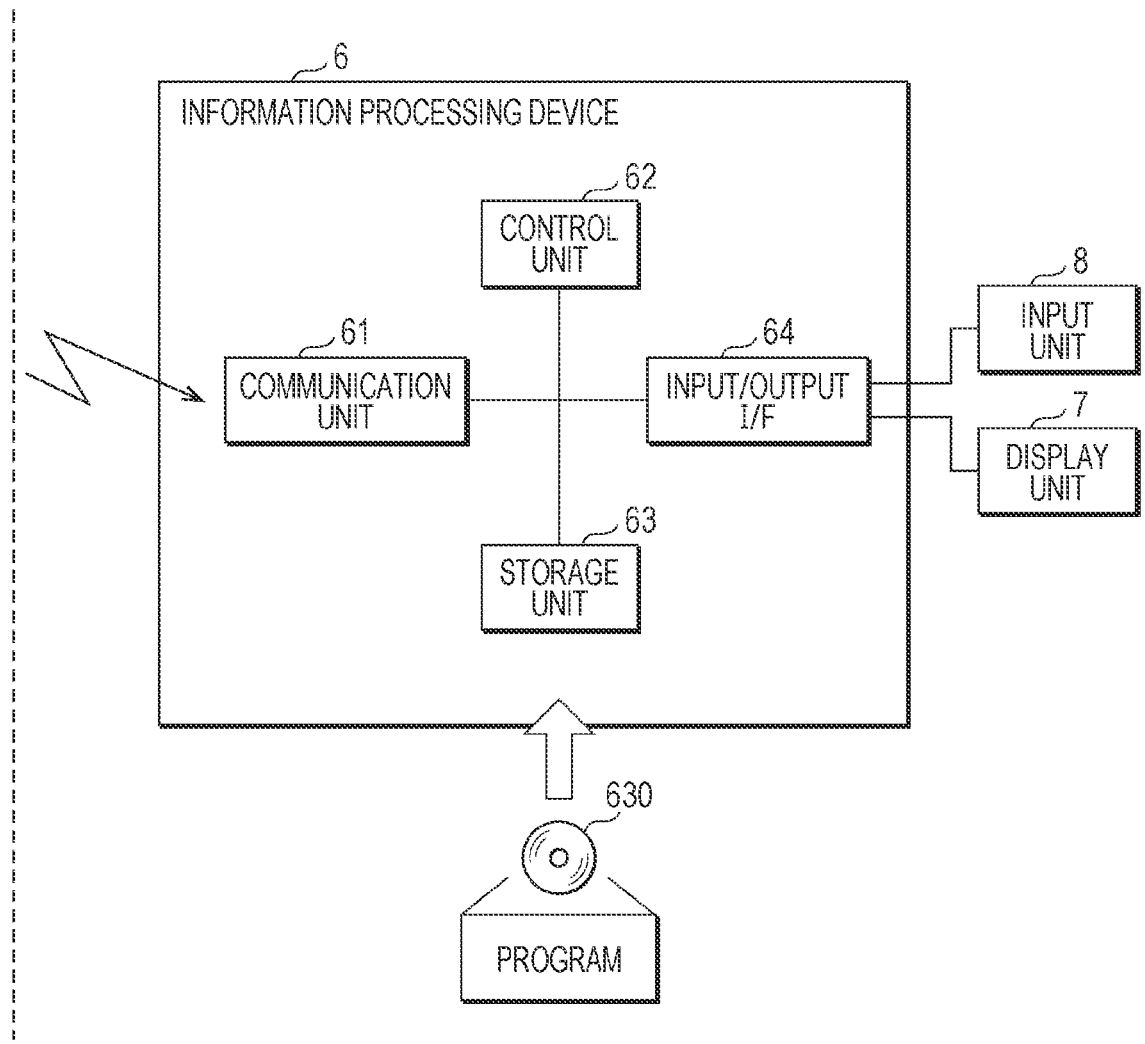
FIG. 3 is a block diagram illustrating a configuration example of an information processing device included in the endoscope system.

FIG. 3 is a block diagram illustrating a configuration example of the information processing device 6 included in the endoscope system. The information processing device 6 includes a control unit 62, a communication unit 61, a storage unit 63, and an input/output I/F 64. The information processing device 6 is, for example, a server device, a personal computer, or the like. The server device includes not only a single server device but also a cloud server device or a virtual server device including a plurality of computers. The information processing device 6 may be provided as a cloud server located on an external network accessible from the processor 20 for an endoscope.

The control unit 62 includes one or a plurality of arithmetic processing devices having a time counting function, such as central processing units (CPUs), micro-processing units (MPUs), and graphics processing units (GPUs), and performs various types of information processing, control processing, and the like related to the information processing device 6 by reading and executing a program P (program product) stored in the storage unit 63. Alternatively, the control unit 62 may include a quantum computer chip, and the information processing device 6 may be a quantum computer.

The storage unit 63 includes a volatile storage area such as a static random access memory (SRAM), a dynamic random access memory (DRAM), or a flash memory and a nonvolatile storage area such as an EEPROM or a hard disk. The storage unit 63 stores in advance the program (program product) and data to be referred to at the time of processing. The program (program product) stored in the storage unit 63 may be a program (program product) which is stored by being read from a recording medium 630 readable by the information processing device 6. In addition, the program (program product) may be a program which is downloaded from an external computer (not illustrated) connected to a communication network (not illustrated) and is stored in the storage unit 63. The storage unit 63 stores an entity file (instance file of a neural network (NN)) constituting a learning model (lesion learning model 631 and region-of-interest learning model 632) to be described later. These entity files may be configured as a part of the program (program product).

The communication unit 61 is a communication module or a communication interface for performing communication with the endoscope device 10 in a wired or wireless manner and is, for example, a narrow-area wireless communication module such as Wi-Fi (registered trademark) or Bluetooth (registered trademark) or a wide-area wireless communication module such as 4G or LTE.

The input/output I/F 64 is a communication interface conforming, for example, to a communication standard such as USB or DSUB and is a communication interface for performing serial communication with an external device connected to the input/output I/F 64. For example, a display unit 7 such as a display and an input unit 8 such as a keyboard are connected to the input/output I/F 64, and the control unit 62 outputs, to the display unit 7, a result of information processing performed based on an execution command or an event input from the input unit 8.

Figure 4:
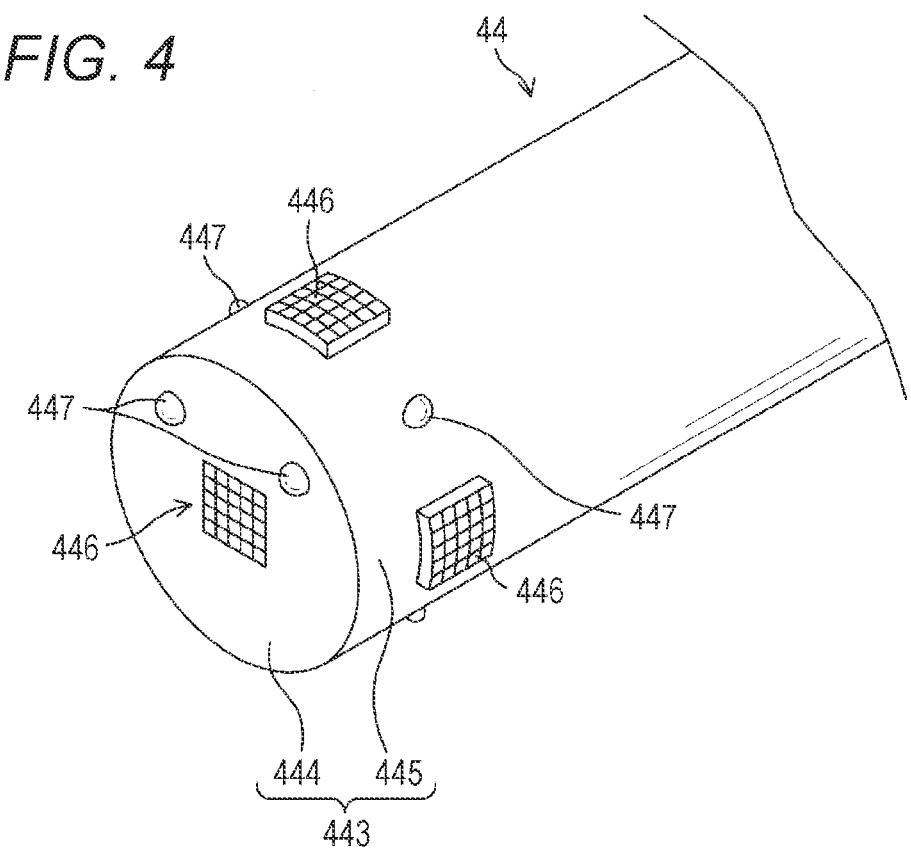
FIG. 4 is a perspective view schematically illustrating a distal end portion (peripheral surface) of an insertion portion.
Figure 5:
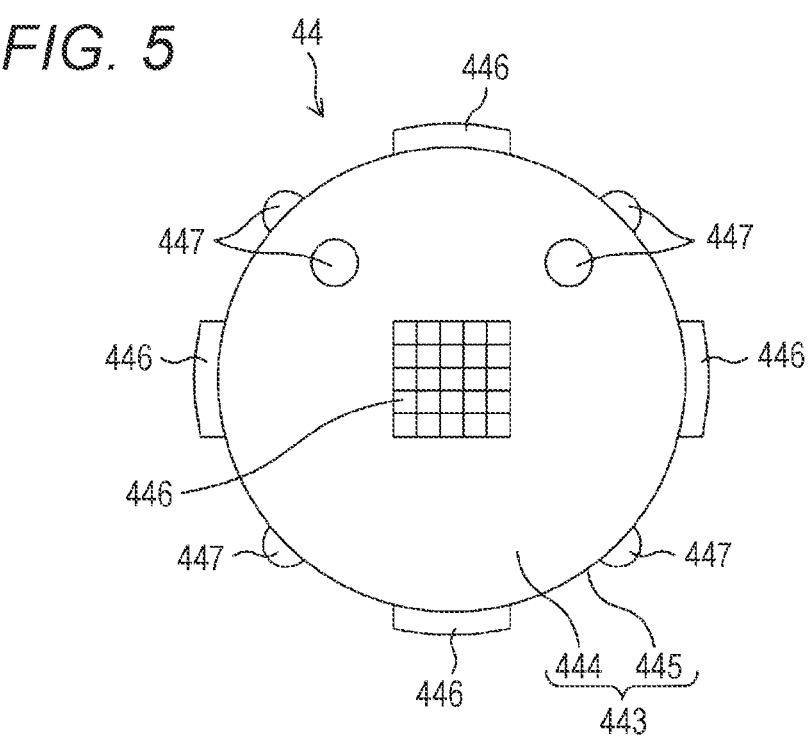
FIG. 5 is a front view schematically illustrating the distal end portion (end surface) of the insertion portion.

FIG. 4 is a perspective view schematically illustrating a distal end portion (peripheral surface 445) of the insertion portion. FIG. 5 is a front view schematically illustrating a distal end portion (end surface 444) of the insertion portion. The distal end portion 443 of the endoscope 40 is provided with a plurality of imaging units 446 and imaging light sources 447.

The plurality of imaging units 446 includes the imaging units 446 (four units in the drawings) equally arranged along the circumferential direction on the peripheral surface 445 of the cylindrical body in the distal end portion 443 and the imaging unit 446 (one unit in the drawings) provided on the end surface 444 of the cylindrical body in the distal end portion 443. The imaging unit 446 includes, for example, an imaging sensor such as a CMOS and a substrate on which the image sensor is mounted. The substrate on which the image sensor is mounted (imaging unit 446) and the processor 20 for an endoscope are connected via, for example, a communication line and an electrical connector 311.

The imaging unit 446 provided on the end surface 444 of the cylindrical body in the distal end portion 443 captures an image of a front area with respect to the insertion direction of the endoscope 40. Each of the plurality of imaging units 446 provided on the peripheral surface 445 of the cylindrical body at the distal end portion 443 captures an image of a side area in the insertion direction of the endoscope 40. That is, each of the plurality of imaging units 446 provided on the peripheral surface 445 of the cylindrical body at the distal end portion 443 can capture images of intracorporeal sites positioned behind an intracorporeal site whose image is captured by the imaging unit 446 provided on the end surface 444 of the cylindrical body at the distal end portion 443 in the insertion direction of the endoscope 40. According to the present embodiment, the number of the imaging units 446 provided on the peripheral surface of the tubular distal end portion 443 is four, and the respective imaging units 446 are arranged at equal intervals every 90 degrees of the circumferential angle, but the present invention is not limited thereto. The number of imaging units 446 provided on the peripheral surface of the tubular distal end portion 443 may be, for example, three arranged at equal intervals every 120 degrees of the circumferential angle.

The plurality of imaging light sources 447 include image capturing light sources 447 (four sources in the drawings) arranged at equal intervals along the circumferential direction on the peripheral surface 445 of the cylindrical body at the distal end portion 443, and an imaging light sources 447 (two sources in the drawings) provided on the end surface 444 of the cylindrical body at the distal end portion 443. The imaging light source 447 may be an illumination light emitted from the light source 33 guided by the fiber bundle through the illumination window provided in the distal end portion 443, or may be a white LED or the like provided in the distal end portion 443. In a case where the white LED is provided at the distal end portion 443, it is possible to eliminate the need for the light source 33 included in the endoscope device. Since the plurality of imaging light sources 447 are provided corresponding to the imaging unit 446 provided on the end surface 444 of the cylindrical body at the distal end portion 443 and the plurality of imaging units 446 provided on the peripheral surface 445 of the cylindrical body at the distal end portion 443, respectively, it is possible to supply a sufficient quantity of light when the plurality of imaging units 446 capture images of the intracorporeal sites.

By providing the plurality of imaging units 446 on the peripheral surface 445 of the cylindrical body and the end surface 444 of the cylindrical body at the distal end portion 443 in this manner, it is possible to acquire a plurality of endoscopic images obtained in a plurality of different viewpoint directions at a single (same) viewpoint position.

Figure 6:
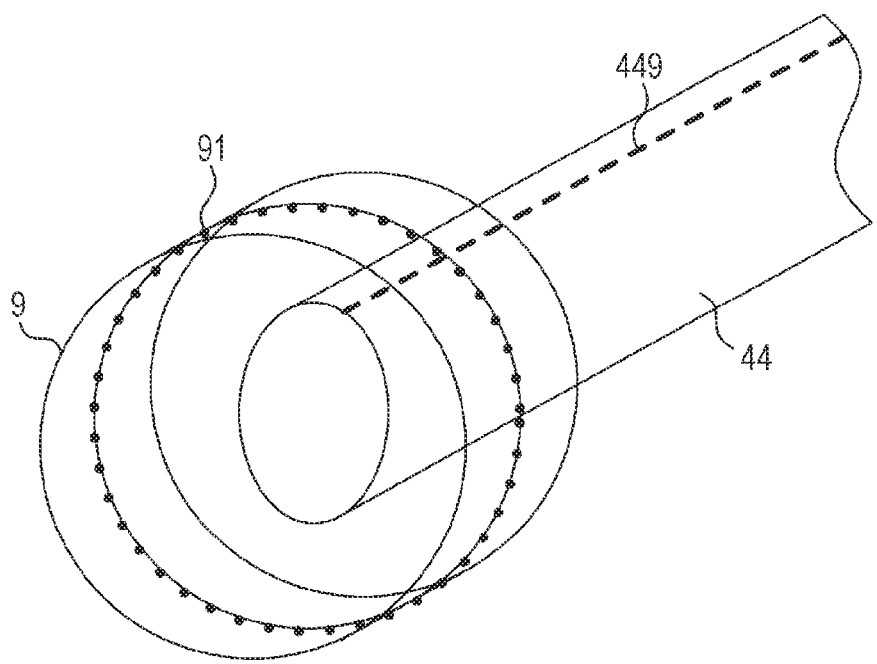
FIG. 6 is an explanatory diagram schematically illustrating a measurement unit.

FIG. 6 is an explanatory diagram schematically illustrating a measurement unit 9 (mouthpiece, attachment). The measurement unit 9 is configured as, for example, a mouthpiece attached to an oral portion or an attachment attached to an anal portion, and is an annular member in which a hole portion for inserting the insertion portion 44 of the endoscope 40 is formed.

The annular measurement unit 9 is provided with a detection unit 91 along the circumferential direction. The detection unit 91 includes an optical sensor or a magnetic sensor. A detection target 449 corresponding to the detection unit 91 is provided in the insertion portion 44 of the endoscope 40.

The detection target 449 is an elongated body provided along the axial direction of the insertion portion 44 of the endoscope 40, and is detected by the detection unit 91 including an optical reflection member, a magnetic body, or the like and including an optical sensor, a magnetic sensor, or the like.

When the insertion portion 44 of the endoscope 40 passes through the measurement unit 9 and is inserted into the body, the measurement unit 9 detects (senses) the detection target 449 provided with the insertion portion 44 to derive the insertion distance of the insertion portion 44 of the endoscope 40 and the rotation angle of the insertion portion 44, and outputs the derived insertion distance and rotation angle to the processor for the endoscope 40. In other words, the measurement unit 9 functions as an insertion distance measurement unit and a rotation angle measurement unit.

When inserted into the body, the insertion portion 44 of the endoscope 40 passes through a mouthpiece (measurement unit 9) attached to the oral cavity portion in the case of upper endoscopy, and an attachment (measurement unit 9) attached to the anal portion in the case of lower endoscopy, and is inserted into the body. Therefore, in any case, the insertion distance of the insertion portion 44 of the endoscope 40 and the rotation angle of the insertion portion 44 can be suitably derived.

According to the present embodiment, the measurement unit 9 including the mouthpiece or the attachment is used to measure the rotation angle of the insertion portion 44, but the present invention is not limited thereto. A gyroscope or an acceleration sensor may be provided in the operation unit 43 of the endoscope 40, the rotation amount of the operation unit 43 may be measured, and the rotation angle of the insertion portion 44 may be derived on the basis of the measured rotation amount.

Figure 7:
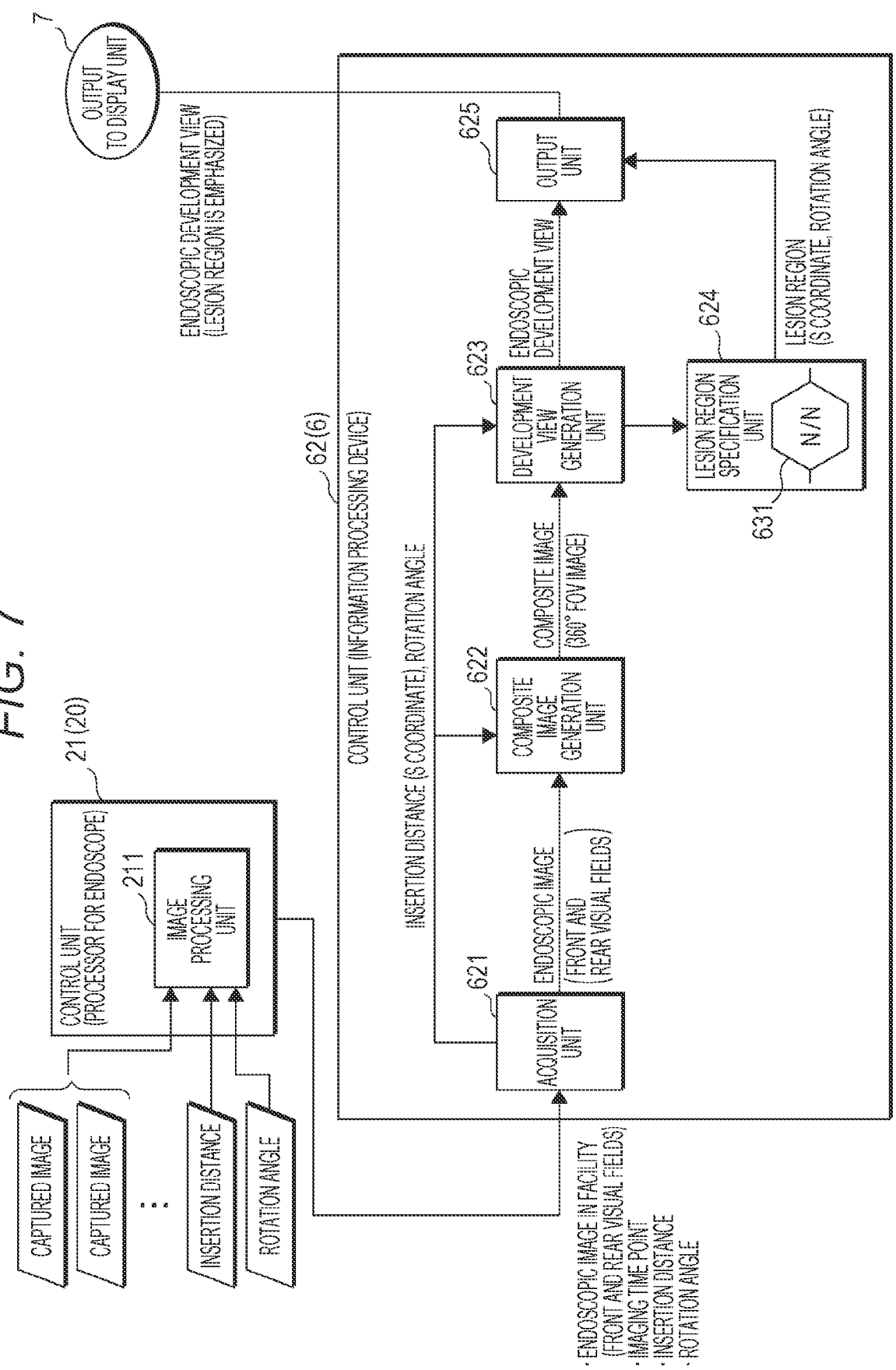
FIG. 7 is a functional block diagram exemplifying functional units included in a control unit of the information processing device.

FIG. 7 is a functional block diagram exemplifying functional units included in the control unit 62 of the information processing device 6. The control unit 21 of the processor 20 for an endoscope (endoscope device 10) executes the program stored in the main storage device 22, thereby functioning as the image processing unit 211. The control unit 62 of the information processing device 6 functions as an acquisition unit 621, a composite image generation unit 622, a development view generation unit 623, a lesion region specification unit 624 (lesion learning model 631), and an output unit 625 by executing a program stored in the storage unit 63.

The image processing unit 211 of the processor 20 for an endoscope performs various types of image processing such as gamma correction, white balance correction, and shading correction on the image (a plurality of captured images) output from the endoscope 40 (captured by a plurality of imaging units 446), and outputs the image as a plurality of endoscopic images. The image processing unit 211 outputs (transmits) the generated endoscopic image and the examination date and time based on an imaging time point of the endoscopic image to the information processing device 6. The image processing unit 211 may further output the subject ID which is input from the keyboard 15 to the information processing device 6.

The processor 20 for an endoscope (image processing unit 211) outputs, to the information processing device 6, information regarding the insertion distance (S coordinate) and the rotation angle of the endoscope 40 output from a sensor such as the measurement unit 9 (mouthpiece, attachment) provided for the insertion portion 44 (flexible tube) of the endoscope 40 in order to measure the surrounding environment of the endoscope 40. The image processing unit 211 may superimpose the information on the insertion distance and the rotation angle of the endoscope 40 acquired from the measurement unit 9, for example, on the endoscopic image and display the superimposed image on the display device 50.

Figure 8:
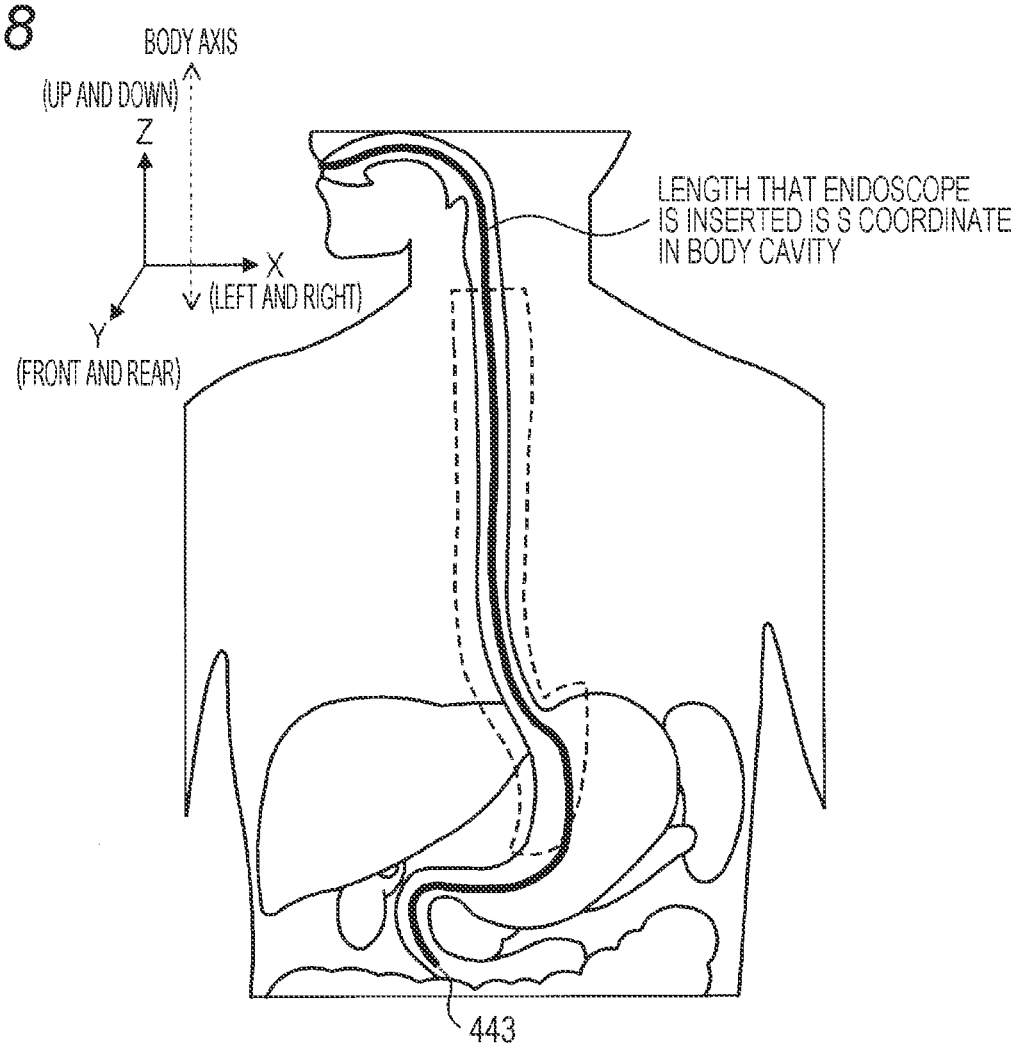
FIG. 8 is an explanatory diagram illustrating an insertion distance (a value of an S coordinate) of the endoscope.

The acquisition unit 621 acquires the plurality of endoscopic images, the S coordinate (insertion distance), and the rotation angle output from the processor 20 for an endoscope, FIG. 8 is an explanatory diagram illustrating an insertion distance (a value of an S coordinate) of the endoscope 40. As illustrated, in a case where the digestive organ or the like photographed by the endoscope 40 is expressed by a three-dimensional shape, a space is formed inside the inner wall of the digestive organ or the like, and the space serves as an insertion path into which the endoscope 40 is inserted. The S coordinate, which is the insertion distance of the endoscope 40 (insertion portion 44), corresponds to a location which is on the inner side of the insertion path (the inner side of the inner wall of the digestive organ) and in which a path length of the insertion path is substantially equal to the insertion distance. Thus, the coordinate of the distal end portion 443 of the endoscope 40 located on the inner side of the inner wall of the digestive organ can be derived based on the S coordinate.

Regarding the rotation angle of the endoscope 40 (insertion portion 44), in a case where the Z axis is defined to be parallel to the body axis of the subject, the Z axis indicates the vertical direction, the Y axis indicates the front-back direction, and the Z axis indicates the left-right direction, and the rotation angle is defined with these axes as rotation axes. The rotation angle when the endoscopic image is captured by the upper endoscopy is an angle with a vertical direction (Z axis) parallel to the body axis of the subject as a rotation axis, and the rotation angle when the endoscopic image is captured by the lower endoscopy is an angle with a front-back direction parallel to the longitudinal direction of the body cavity of the subject as a rotation axis.

The acquisition unit 621 outputs the plurality of acquired endoscopic images, the S coordinate (insertion distance), and the rotation angle to the composite image generation unit 622. When outputting these to the composite image generation unit 622, the acquisition unit 621 may output the S coordinate (insertion distance) and the rotation angle in association with each of the plurality of endoscopic images. The plurality of endoscopic images may be endoscopic images captured at the same imaging time point by the imaging units 446 provided at the distal end portion 443 (end surface 444, peripheral surface 445), and the acquisition unit 621 may associate the imaging time point (time information) with each of the plurality of endoscopic images and output the endoscopic images to the composite image generation unit 622. On the basis of a subject ID output from the processor 20 for an endoscope, for example, the acquisition unit 621 may acquire a virtual endoscopic image of the subject ID and a development view of the virtual endoscopic image from a CT device or the like (X-ray CT), which is communicably connected. The virtual endoscopic image is an image which is generated (reconstructed) based on the three-dimensional medical image of X-ray CT, MRI, or X-ray cone beam CT and in which the inside of an organ (the inside of a body cavity) in the three-dimensional medical image is represented by a virtual endoscope. On the basis of the virtual endoscopic image, a development view is generated by developing with a vertical axis as a rotation angle and a horizontal axis as an insertion distance. The development view (development view of the virtual endoscopic image) includes regions corresponding to the plurality of endoscopic images acquired by the acquisition unit 621 The acquisition unit 621 outputs the development view of the virtual endoscopic image acquired from the X-ray CT to the output unit 625.

Figure 9:
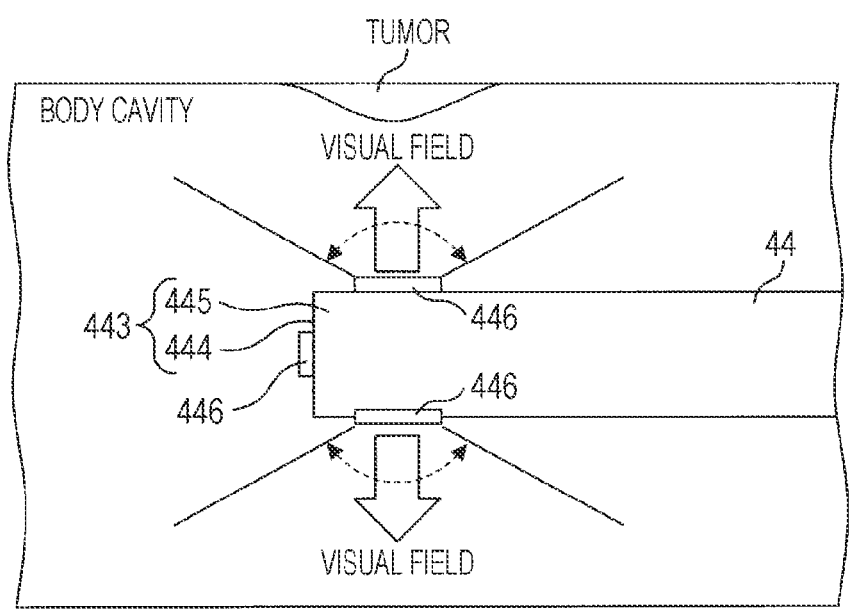
FIG. 9 is an explanatory diagram schematically illustrating image capturing by imaging units provided at the distal end portion of the insertion portion.

The composite image generation unit 622 generates a composite image (360 degree fOV image) having the entire circumference (360 degrees) with respect to the distal end portion 443 including the front and rear in the advancing direction of the insertion portion 44 in the visual field on the basis of the acquired plurality of endoscopic images. FIG. 9 is an explanatory diagram schematically illustrating image capturing by the imaging units 446 provided at the distal end portion 443 of the insertion portion 44. As illustrated in the present embodiment, since the imaging units 446 provided at the distal end portion 443 (end surface 444, peripheral surface 445) include the front, side, and rear visual fields with respect to the advancing direction of the insertion portion 44, it is possible to efficiently combine the 360 degree fOV images on the basis of a plurality of acquired endoscopic images. In particular, the imaging units 446 provided on the peripheral surface 445 have visual fields facing the front (upper) of the tumor and can capture images including the front (upper) of the tumor, and it is possible to improve the observation efficiency and improve the accuracy of the diagnosis support information by AI or the like based on the endoscopic images captured in this manner.

The composite image generation unit 622 may perform geometric correction on individual endoscopic images when combining a plurality of endoscopic images. The geometric correction is, for example, spherical correction using curved surface projection (projection transformation) for projecting acquired endoscopic images onto a continuous curved surface. Alternatively, the geometric correction may be performed on the basis of an image processing algorithm such as affine transformation, pseudo-affine transformation, quadratic conformal transformation, or two-dimensional projective transformation, for example Alternatively, the geometric correction may perform optical simulation on a wide variety of imaged objects on the basis of the specification or optical characteristics of the lens included in the imaging unit 446, generate a dictionary corresponding to the position of the captured image by performing machine learning of the result by artificial intelligence, and perform correction by restoring the dictionary to aberration-free. By performing the geometric correction, it is possible to improve the extraction accuracy of the overlapping region (overlapping region) in the plurality of endoscopic images and correct the image to an image that can be easily combined (an image of a coordinate system that can be easily connected).

The composite image generation unit 622 generates a composite image by superimposing and aligning overlapping regions (regions where the same observation object is imaged) in a plurality of geometrically corrected endoscopic images. The composite image generation unit 622 may associate the generated composite image with an insertion distance and a rotation angle of the endoscope 40 at a time point at which a plurality of endoscopic images as sources of the composite image is captured, and may further associate time information regarding a time point (imaging time point) at which a plurality of endoscopic images as sources of the composite image is captured. The composite image generation unit 622 outputs the generated composite image to the development view generation unit 623.

Figure 10:
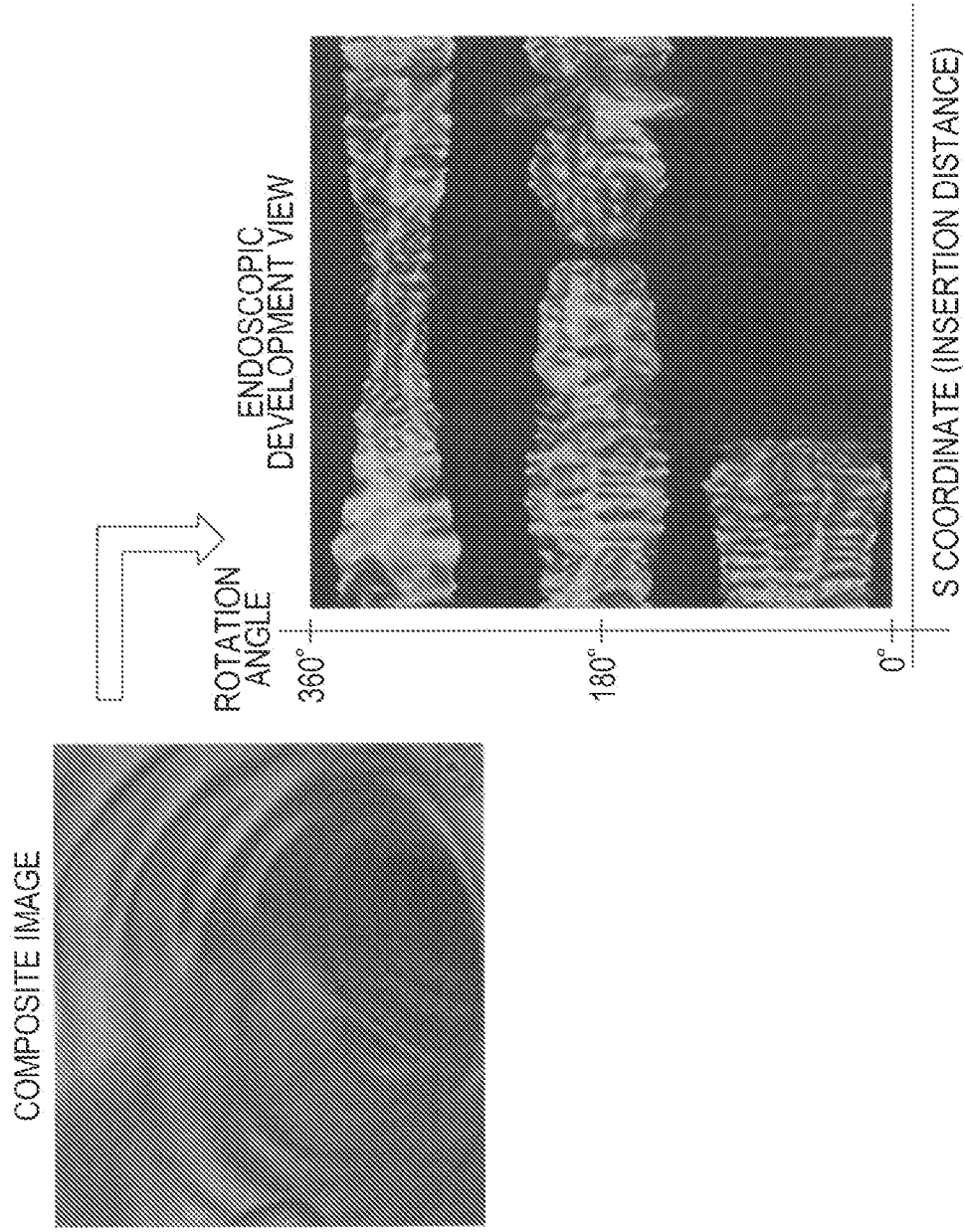
FIG. 10 is an explanatory diagram related to an endoscopic development view.

The development view generation unit 623 generates an endoscopic development view in which the vertical axis represents the rotation angle (second axis) and the horizontal axis represents the insertion distance (first axis) on the basis of the acquired composite image and the insertion distance and the rotation angle associated with the composite image. FIG. 10 is an explanatory diagram related to an endoscopic development view. As illustrated in the present embodiment, it is possible to improve the visibility of the imaged observation site by converting the composite images into the endoscopic development view. In a case where a plurality of composite images having different imaging time points is acquired, the development view generation unit 623 may align a plurality of endoscope development diagrams developed on the basis of the plurality of composite images on the basis of the rotation angle and display the endoscopic development views side by side in accordance with the elapsed order of the imaging time points (order of the insertion distance). The development view generation unit 623 outputs the generated endoscopic development view to the lesion region specification unit 624 and the output unit 625 Note that, in the endoscopic development view, the vertical axis represents the rotation angle, and the horizontal axis represents the insertion distance. However, the horizontal axis may represent (develop) the rotation angle, and the vertical axis may represent the insertion distance.

The lesion region specification unit 624 includes the lesion learning model 631 that outputs a lesion region such as a tumor when an endoscopic image is input. The lesion region specification unit 624 determines whether or not a lesion such as a tumor is included in the endoscopic development view by inputting the acquired endoscopic development view to the lesion learning model 631. Since the endoscopic development view is an image formed by combining a plurality of endoscopic images, it is possible to acquire whether or not a lesion such as a tumor is included in the endoscopic development view by inputting the endoscopic development view to the lesion learning model 631. In a case where a tumor or the like is included, the lesion region specification unit 624 specifies the region (tumor region) of the tumor in the endoscopic development view by an insertion distance and a rotation angle of the endoscope 40, and outputs information regarding the tumor region to the output unit 625.

The lesion learning model 631 is a neural network learned using training data, and is assumed to be used as a program module that is a part of artificial intelligence software. The lesion learning model 631 is used in the information processing device 6 including the control unit 62 (CPU or the like) and the storage unit 63 as described above and is executed by the information processing device 6 having arithmetic processing capability in this way, whereby a neural network system is configured. That is, the control unit 62 of the information processing device 6 operates to perform an arithmetic operation of extracting a feature amount of the endoscopic image input into an input layer according to a command from the lesion learning model 631 stored in the storage unit 63 and output the diagnosis support information including the presence or absence of a lesion and the like from an output layer.

The input layer has a plurality of neurons that receives the input of a pixel value of the endoscopic image, and the input layer transmits the input pixel value and distance information to the intermediate layer. The intermediate layer has a plurality of neurons that extracts an image feature amount of the endoscopic image, and the intermediate layer transfers the extracted image feature amount to the output layer. The output layer has one or a plurality of neurons that outputs information regarding the presence or absence of a lesion and the stage of a symptom, and the output layer outputs information regarding the presence or absence of a lesion and the stage of a symptom on the basis of the image feature amount output from the intermediate layer. For example, in a case where the lesion learning model 631 is a convolutional neural network (CNN), the intermediate layer has a configuration in which a convolution layer that convolves the pixel value of each pixel input from the input layer and a pooling layer that maps (compresses) the pixel value convolved by the convolution layer are alternately connected, and the intermediate layer finally extracts the feature amount of the endoscopic image while compressing pixel information of the endoscopic image. The output layer has one or a plurality of neurons that outputs information regarding the presence or absence of a lesion and the like in the intracorporeal site included in the endoscopic image, and the output layer outputs information regarding the presence or absence of a lesion on the basis of the image feature amount and the like output from the intermediate layer. The output information regarding the presence or absence of a lesion and the like is information used as diagnosis support information by a doctor or the like who operates the endoscope 40.

According to the present embodiment, data to be processed such as data input to the lesion learning model 631 or data to be synthesized is described as an endoscopic image, but the present invention is not limited thereto. The data to be processed may be captured images (raw image) captured by the imaging units 446 of the endoscope 40. That is, the lesion learning model 631 may output information regarding the presence or absence of a lesion and the like when the captured image is input. In the present embodiment, the lesion learning model 631 is described as a neural network (NN) such as a CNN, but the lesion learning model 631 is not limited to the NN and may be a lesion learning model 631 including another learning algorithm such as a support vector machine (SVM), a Bayesian network, or a regression tree. Alternatively, instead of the CNN, any object detection algorithm such as Regions with Convolutional Neural Network (RCNN), Fast RCNN, Faster RCNN, Single Shot Multibook Detector (SSD), or You Only Look Once (YOLO) may be used.

On the basis of the information (insertion distance and rotation angle) regarding the tumor region acquired from the lesion region specification unit 624 and the endoscopic development view acquired from the development view generation unit 623, the output unit 625 outputs a highlighted endoscopic development view, such as displaying a red frame surrounding the tumor region specified in the endoscopic development view in a superimposed manner, to the display unit 7. The display unit 7 displays the highlighted endoscopic development view on the display screen included in the display unit 7 on the basis of the data output from the output unit 625. The output unit 625 may further generate data for displaying the endoscopic development view acquired from the development view generation unit 623 and the development view of the virtual endoscopic image acquired from the X-ray CT via the acquisition unit side by side, and output the data to the display unit 7. Furthermore, the output unit 625 may generate data for displaying the composite image (360 degree fOV image) and the virtual endoscopic image side by side, and output the data to the display unit 7. As described above, since the development view of the virtual endoscopic image acquired from the X-ray CT includes the regions corresponding to the plurality of endoscopic images which are the original data of the endoscopic development view acquired from the development view generation unit 623, these development diagrams include the same observation region. Therefore, it is possible to provide effective diagnosis support information to a doctor or the like by comparing and displaying the development view (endoscopic development view) from the endoscopic images for the same observation site and the development view of the virtual endoscopic image acquired from the X-ray CT side by side.

The display form in which the endoscopic development view and the development view of the virtual endoscopic image are displayed in comparison is not limited to the form in which these development views are displayed side by side, and may be a form in which these development views are displayed in an overlapping manner. For example, in a case where the endoscopic development view is superimposed and displayed on the development view of the virtual endoscopic image, the endoscopic development view may be transformed to be translucent, aligned using the insertion distance (S coordinate) and the rotation angle, and these development views may be superimposed and displayed. Similarly, the composite image (360 degree fOV image) and the virtual endoscopic image may be superimposed and displayed. In addition, when these development views are superimposed and displayed, each of the development views in which a lesion region is specified by the lesion region specification unit 624 (endoscopic development view, development view of virtual endoscopic image) may be superimposed and displayed. Also, regarding the composite image (360 degree fOV image) and the virtual endoscopic image, a lesion region may be specified using AI (learning model) configured by CNN or the like as in the lesion region specification unit 624 or the like, and the composite image (360 degree fOV image) in which the lesion region is specified by annotation display such as a red frame and the virtual endoscopic image may be displayed in an overlapping manner.

In the present embodiment, the respective functional units in a series of processing have been described while being divided into each functional unit implemented by the control unit 21 of the processor 20 for an endoscope and each functional unit implemented by the control unit 62 of the information processing device 6, but the division of these functional units is an example and is not limited thereto. The control unit 21 of the processor 20 for an endoscope may function as all the functional units implemented by the control unit 62 of the information processing device 6. That is, the processor 20 for an endoscope may substantially include the information processing device 6. Alternatively, the control unit 21 of the processor 20 for an endoscope may only output the captured image captured by the imaging unit 446, and the control unit 62 of the information processing device 6 may function as all the functional units that perform the subsequent processing. Alternatively, the control unit 21 of the processor 20 for an endoscope and the control unit 62 of the information processing device 6 may perform, for example, inter-process communication, thereby functioning in cooperation as the respective functional units in the series of processing.

Figure 11:
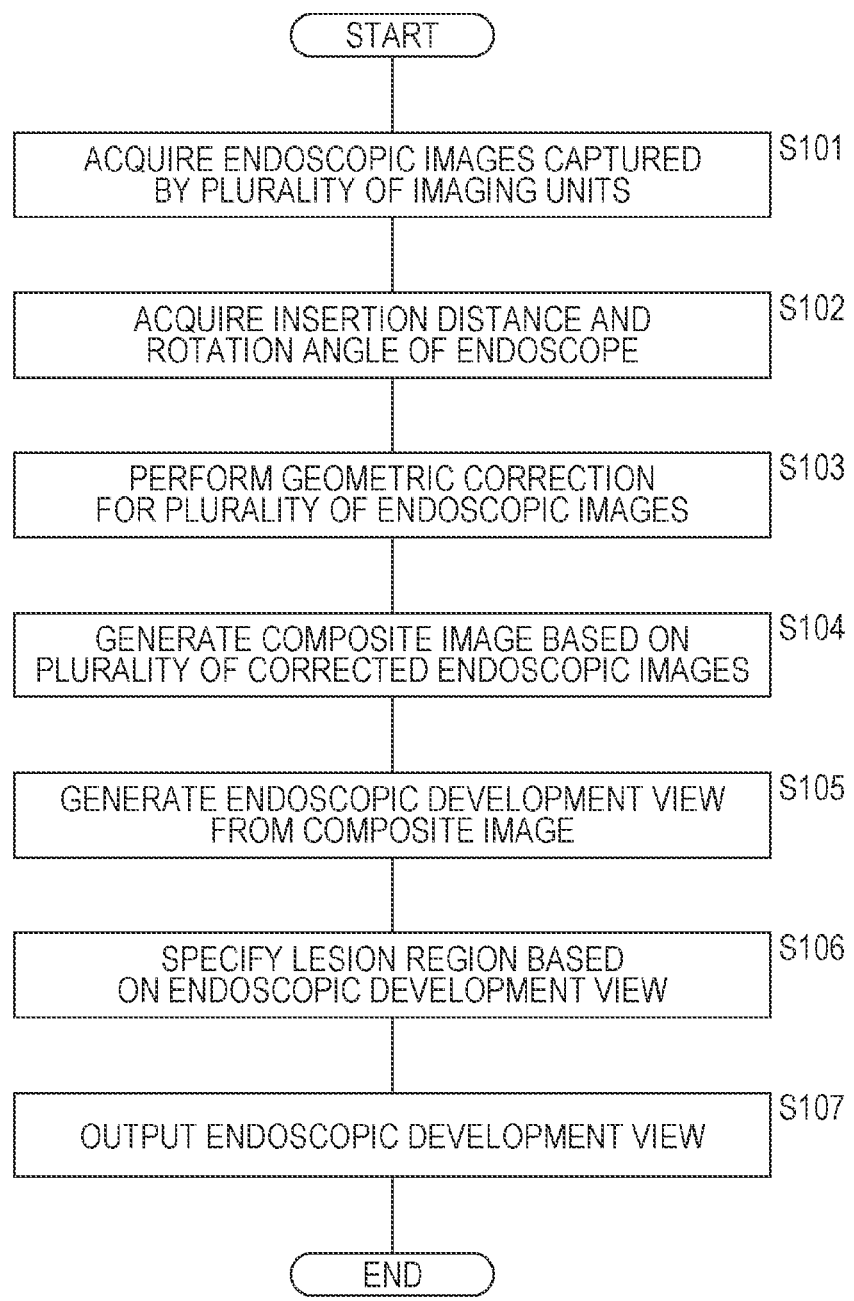
FIG. 11 is a flowchart illustrating an example of a processing procedure in the control unit.

FIG. 11 is a flowchart illustrating an example of a processing procedure by the control unit 62. For example, the information processing device 6 starts processing of the flowchart based on a content input from the input unit 8 connected to the device.

The control unit 62 of the information processing device 6 acquires endoscopic images captured by the plurality of imaging units 446 (S101). Each of the imaging units 446 provided at the distal end portion 443 (end surface 444, peripheral surface 445) includes the front, side, and rear visual fields with respect to the advancing direction of the insertion portion 44, and the control unit 62 of the information processing device 6 acquires a plurality of endoscopic images obtained by imaging observation sites in the front, side, and rear visual field directions with respect to the advancing direction of the insertion portion 44.

The control unit 62 of the information processing device 6 acquires the insertion distance and the rotation angle of the endoscope 40 (S102). The control unit 62 of the information processing device 6 acquires the insertion distance and the rotation angle of the endoscope 40 output from the measurement unit 9 configured as, for example, a mouthpiece, an attachment, or the like. Regarding the rotation angle, the rotation angle is an angle with a vertical direction parallel to the body axis of the subject as a rotation axis when the endoscopic image is captured by upper endoscopy, and the rotation angle is an angle with a front-back direction perpendicular to the body axis of the subject as a rotation axis when the endoscopic image is captured by lower endoscopy.

The control unit 62 of the information processing device 6 performs geometric correction on the plurality of endoscopic images (S103). The control unit 62 of the information processing device 6 performs geometric correction on each of the plurality of acquired endoscopic images to improve extraction accuracy of a region that is overlapped (overlapping region) in the plurality of endoscopic images and correct the endoscopic images to an image that is easy to combine (an image of a coordinate system that is easy to connect). The geometric correction is, for example, spherical correction using curved surface projection (projection transformation) for projecting acquired endoscopic images onto a continuous curved surface. Alternatively, the geometric correction may be performed on the basis of an image processing algorithm such as affine transformation, pseudo-affine transformation, quadratic conformal transformation, or two-dimensional projective transformation, for example. Alternatively, the geometric correction may be performing optical simulation on a wide variety of imaged objects on the basis of the specification or optical characteristics of the lens included in the imaging unit 446, generating a dictionary (lookup table) corresponding to the position of the captured image by performing machine learning of the result by artificial intelligence (AI), and performing correction by restoring the dictionary to aberration-free.

The control unit 62 of the information processing device 6 generates a composite image on the basis of the plurality of corrected endoscopic images (S104). The control unit 62 of the information processing device 6 generates a composite image by superimposing and aligning overlapping regions (regions where the same observation object is imaged) in a plurality of geometrically corrected endoscopic images. The plurality of imaging units 446 is provided on the end surface 444 and the peripheral surface 445 of the distal end portion 443 of the insertion portion 44, and the imaging units 446 provided on the peripheral surface 445 are arranged at equal intervals along the circumferential direction. The imaging unit 446 of the end surface 444 images the front in the advancing direction of the insertion portion 44, and the imaging units 446 of the peripheral surface 445 captures images of the side and the rear with respect to the traveling direction of the insertion portion 44. Therefore, by combining a plurality of endoscopic images captured by the plurality of imaging units 446, it is possible to generate a composite image (360 degree fOV image) having the entire circumference (360 degrees) with respect to the distal end portion 443 including the front and rear visual fields with respect to the advancing direction of the insertion portion 44.

The control unit 62 of the information processing device 6 associates the generated composite image with the insertion distance and the rotation angle of the endoscope 40 at the time of capturing the plurality of endoscopic images that are the sources of the composite image. The control unit 62 of the information processing device 6 may further associate time information regarding a time point (imaging time point) at which the plurality of endoscopic images serving as sources of the composite image is captured with the generated composite image.

The control unit 62 of the information processing device 6 generates an endoscopic development view from the composite image (S105). The control unit 62 of the information processing device 6 generates an endoscopic development view in which the vertical axis represents the rotation angle and the horizontal axis represents the insertion distance on the basis of the composite image and the insertion distance and the rotation angle associated with the composite image. The control unit 62 of the information processing device 6 may align the endoscopic development views generated from the individual composite images on the basis of the plurality of composite images on the basis of the rotation angle, and arrange and display the endoscopic development views according to the order of the insertion distances (the order of progress of the imaging time points).

The control unit 62 of the information processing device 6 specifies a lesion region on the basis of the endoscopic development views (S106). The control unit 62 of the information processing device 6 determines whether a lesion such as a tumor is included in the endoscopic development view by inputting the endoscopic development view to the lesion learning model 631 using, for example, the lesion learning model 631 stored in the storage unit 63 of the device, and in a case where a tumor is included, specifies a region (tumor region) of the tumor in the endoscopic development view by an insertion distance and a rotation angle of the endoscope 40.

The control unit 62 of the information processing device 6 outputs an endoscopic development view in which a lesion region is highlighted (S107). In a case where a lesion such as a tumor is included, the control unit 62 of the information processing device 6 outputs, to the display unit 7, an endoscopic development view highlighted, for example, by superimposing and displaying a red frame surrounding the specified tumor region on the endoscopic development view. The display unit 7 displays the endoscopic development view highlighted on the display screen included in the display unit 7 on the basis of the data output.

According to the present embodiment, the series of processing is performed by the control unit 62 of the information processing device 6, but the present invention is not limited thereto. The series of processing may be performed by the control unit 21 of the processor 20 for an endoscope. Alternatively, the series of processing may be performed in cooperation between the control unit 21 of the processor 20 for an endoscope and the control unit 62 of the information processing device 6, for example, by performing inter-process communication.

According to the present embodiment, since the plurality of imaging units 446 is provided on the end surface 444 and the peripheral surface 445 of the tubular distal end portion 443 provided in the insertion portion 44 of the endoscope 40, a plurality of endoscopic images including a front visual field and a rear visual field with respect to the distal end portion 443 can be acquired from each of the plurality of imaging units 446. It is possible to efficiently generate a composite image in the entire circumferential direction including the front visual field and the rear visual field with respect to the distal end portion 443 on the basis of the plurality of acquired endoscopic images. Since the composite image is obtained by combining the plurality of endoscopic images captured by the plurality of imaging units 446 on the end surface 444 and equally arranged at a predetermined circumferential angle on the peripheral surface 445 of the distal end portion 443, the composite image is relevant to a 360 degree field of view (FOV) image including a visual field over the entire circumference in the circumferential direction of the tubular distal end portion 443.

The endoscopic images are captured by the plurality of imaging units 446 at a plurality of time points. At this time, by associating the insertion distance and the rotation angle of the endoscope 40 at the time when the endoscopic image is captured with the composite image, it is possible to specify the position (coordinates) in the body of the generated composite image on the basis of the insertion distance and the rotation angle. In other words, by assigning (associating) absolute coordinates to each of the captured endoscopic images, these images can be compared (endoscopic image comparison) by matching the rotation directions. Therefore, it is possible to efficiently perform coordinate reproducibility and comparison (comparison in a time direction) over time for each of the endoscopic images (360 degree fOV images) of the 360 degree field of view captured at a plurality of time points.

According to the present embodiment, the endoscope 40 includes, for example, the endoscope 40 for upper gastrointestinal endoscopy such as a gastric camera and the endoscope 40 for lower gastrointestinal endoscopy such as a colon camera. The insertion distance in a case where the endoscopic image is captured by upper endoscopy is an insertion distance output from the measurement unit 9 (mouthpiece) provided in the oral cavity portion of the subject, and the insertion distance in a case where the endoscopic image is captured by lower endoscopy is an insertion distance output from the measurement unit 9 (attachment) provided in the anal portion of the subject. The rotation angle when the endoscopic image is captured by the upper endoscopy is an angle with a vertical direction parallel to the body axis of the subject as a rotation axis, and the rotation angle when the endoscopic image is captured by the lower endoscopy is an angle with a front-back direction parallel to the longitudinal direction of the body cavity of the subject as a rotation axis. The measurement unit 9 is, for example, a mouthpiece attached to the oral cavity portion of the subject or an attachment attached to the anal portion of the subject, and functions as an insertion distance measuring unit that measures an insertion distance measurement unit and a rotation angle measurement unit that measures a rotation angle. Therefore, the insertion distance and the rotation angle can be appropriately detected (measured) in either case of the upper endoscopy or the lower endoscopy.

According to the present embodiment, a plurality of composite images can be generated on the basis of endoscopic images captured at a plurality of time points. The plurality of generated composite images is captured at different time points, and the insertion distance and the rotation angle of the endoscope 40 are different according to the time points. On the basis of such a plurality of composite images, by generating an endoscopic development view in which the insertion distance of the endoscope 40 is set to the horizontal axis and the rotation angle is set to the vertical axis, it is possible to efficiently generate an endoscopic development view with excellent visibility. The plurality of composite images is captured at different time points (imaging time points), and the insertion distances and the rotation angles of the endoscope 40 at those imaging time points are different. However, in accordance with the viewing angles of the imaging units 446, there is an overlapping region in which the same observation site is redundantly captured in the plurality of composite images. Therefore, by extracting the overlap region and superimposing the extracted overlapping regions, it is possible to efficiently generate the endoscopic development view in which the lack and the overlap are reduced. By using the endoscopic development view, for example, a tumor can be observed from above with respect to the synthesized 360 degree endoscopic image (360 degree fOV image), and all shadows due to folds of the tumor or the like can be visually recognized, and it is possible to provide effective diagnosis support information to an operator of the endoscope 40 such as a doctor.

According to the present embodiment, in a case where an endoscopic image is input, the endoscopic development view is input to the lesion learning model 631 that outputs a region of a lesion such as a tumor, thereby determining whether or not the endoscopic development view includes a lesion such as a tumor. In a case where a tumor is included, a region of the tumor (tumor region) in the endoscope deployment view is specified by an insertion distance and a rotation angle of the endoscope 40, and the endoscopic development view is output with highlights, for example, a red frame surrounding the specified tumor region is displayed in a superimposed manner. Therefore, it is possible to provide effective diagnosis support information to an operator of the endoscope 40 such as a doctor.

Second Embodiment

Figure 12:
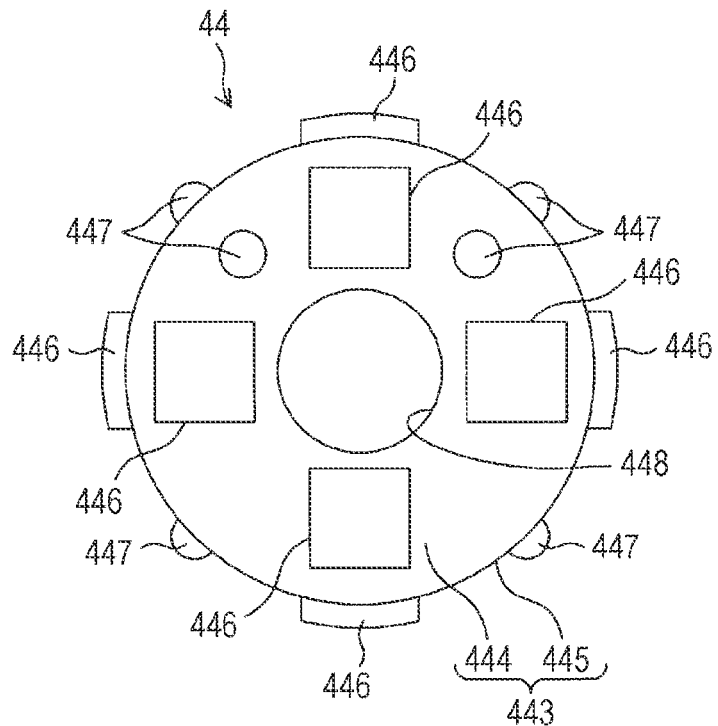
FIG. 12 is a front view schematically illustrating the distal end portion (end surface) of the insertion portion according to a second embodiment (imaging units around a channel).
Figure 13:
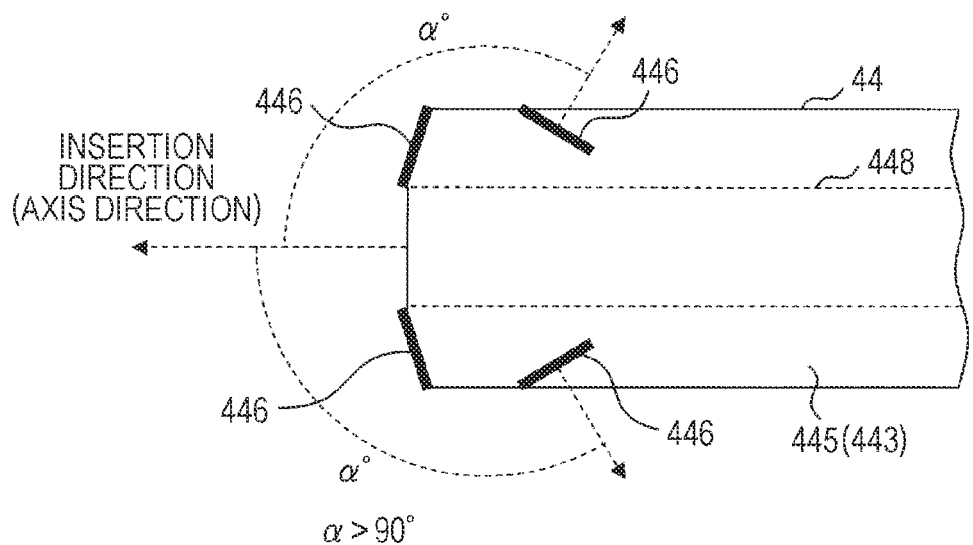
FIG. 13 is a side view schematically illustrating the distal end portion (peripheral surface) of the insertion portion.

An endoscope 40 according to a second embodiment is different from that of the first embodiment in that the plurality of imaging units 446 is provided on the end surface 444 of the distal end portion 443. FIG. 12 is a front view schematically illustrating the distal end portion 443 (the end surface 444) of the insertion portion 44 according to the second embodiment (the imaging units 446 around a channel 448), FIG. 13 is a side view schematically illustrating the distal end portion 443 (peripheral surface 445) of the insertion portion 44.

The endoscope 40 according to the second embodiment includes the plurality of imaging units 446 provided on the end surface 444 and the peripheral surface 445 of the distal end portion 443 having a tubular shape, as in the endoscope 40 according to the first embodiment. The channel 448 (working channel) is provided in a central portion of the end surface 444 of the distal end portion 443 of the endoscope 40 according to the second embodiment.

The channel 448 (working channel) is a hole portion for inserting a treatment tool such as forceps, and extends from the end surface 444 of the distal end portion 443 toward the operation unit 43 so as to penetrate the entire insertion portion 44. The plurality of imaging units 446 is provided on the end surface 444 around the channel 448 provided at the central portion of the end surface 444. The plurality of imaging units 446 provided on the end surface 444 is, for example, four units, and is arranged at the same central angle (90 degrees in the present embodiment) so as to be at equal intervals.

The plurality of imaging units 446 provided on the peripheral surface 445 of the distal end portion 443 is inclined such that the angles of the optical axis of the imaging units 446 are larger than 90 degrees with respect to the insertion direction of the insertion portion 44 of the endoscope 40. The insertion direction of the insertion portion 44 of the endoscope 40 is a direction parallel to the axial direction of the insertion portion 44, and corresponds to an advancing direction (front) when the insertion portion 44 is inserted into the body. As illustrated in the present embodiment, by inclining the imaging units 446 on the peripheral surface 445 rearward, the angles (a) between the insertion direction (axial direction) of the insertion portion 44 and the optical axes of the imaging units 446 on the peripheral surface 445 are larger than 90 degrees ($\alpha° > 90°$). The angles of the optical axes of the imaging units 446 are smaller than 180 degrees with respect to the insertion direction of the insertion portion 44 of the endoscope 40, that is, the angle range is ($180° > \alpha° < 90°$).

According to the present embodiment, since the plurality of imaging units 446 for imaging the front visual field with respect to the distal end portion 443 is provided around the channel 448 provided at the central portion of the end surface 444 of the distal end portion 443 so as to be at equal intervals, for example, the diameter of the distal end portion 443, that is, the insertion portion 44 of the endoscope 40 can be reduced. Since the angles of the optical axes of the imaging units 446 arranged on the peripheral surface 445 of the distal end portion 443 are larger than 90 degrees with respect to the insertion direction when the insertion portion 44 of the endoscope 40 is inserted into the body, the optical axes of the imaging units 446 on the peripheral surface 445 face rearward with respect to the insertion direction of the insertion portion 44. Therefore, the imaging units 446 on the peripheral surface 445 can image rear visual fields having a wider range.

Third Embodiment

Figure 14:
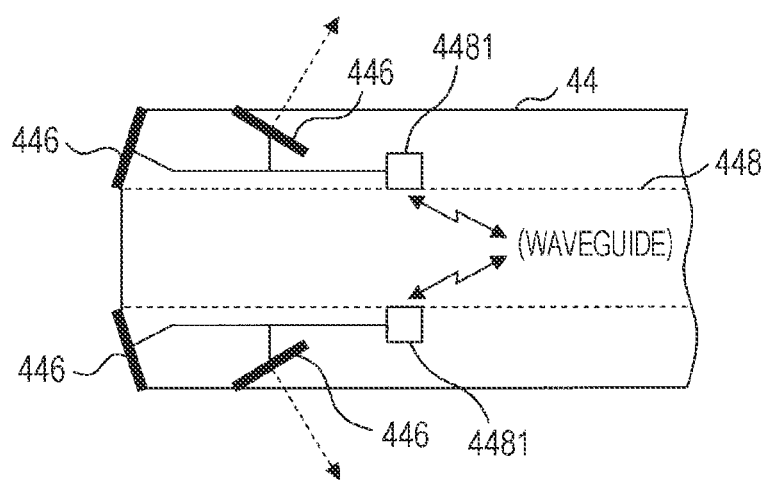
FIG. 14 is a side view schematically illustrating the distal end portion (peripheral surface) of the insertion portion according to a third embodiment (wireless communication unit/waveguide)

An endoscope 40 according to a third embodiment is different from that of the first embodiment in that captured images output from imaging units 446 are transmitted by using wireless communication. FIG. 14 is a side view schematically illustrating the distal end portion 443 (peripheral surface 445) of the insertion portion 44 according to the third embodiment (wireless communication unit 4481/waveguide).

The distal end portion 443 of the endoscope 40 is provided with wireless communication units 4481 that are connected to the imaging units 446 by lead wires or the like and wirelessly transmit the captured images output from the imaging units 446. The wireless communication units 4481 are arranged on the outer peripheral surface of the channel 448, for example, and wirelessly transmit the captured images output by the imaging units 446 to the communication unit 24 of the processor for the endoscope 40. In this case, the communication unit 24 of the processor for the endoscope 40 functions as a reception unit of wireless communication.

The wireless communication units 4481 may radiate radio waves into a space formed by the inner wall of the channel 448 using the channel 448 as a waveguide, and transmit captured images output by the imaging units 446 to a reception unit of wireless communication provided in the operation unit 43.

According to the present embodiment, the outputs of the endoscopic image from the imaging units 446 provided in the endoscope 40 to the control unit 62 provided in the processor for the endoscope 40 are performed by wireless communication between the endoscope 40 and the processor for the endoscope 40. Therefore, it is not necessary to provide wiring for transmitting the images captured by the imaging units 446 inside the insertion portion 44 of the endoscope 40, and the diameter of the insertion portion 44 of the endoscope 40 can be reduced. Furthermore, by using the channel 448 (working channel) configured by a hole portion penetrating the entire insertion portion 44 as a waveguide, the radio waves of wireless communication can be suitably propagated.

Fourth Embodiment

Figure 15:
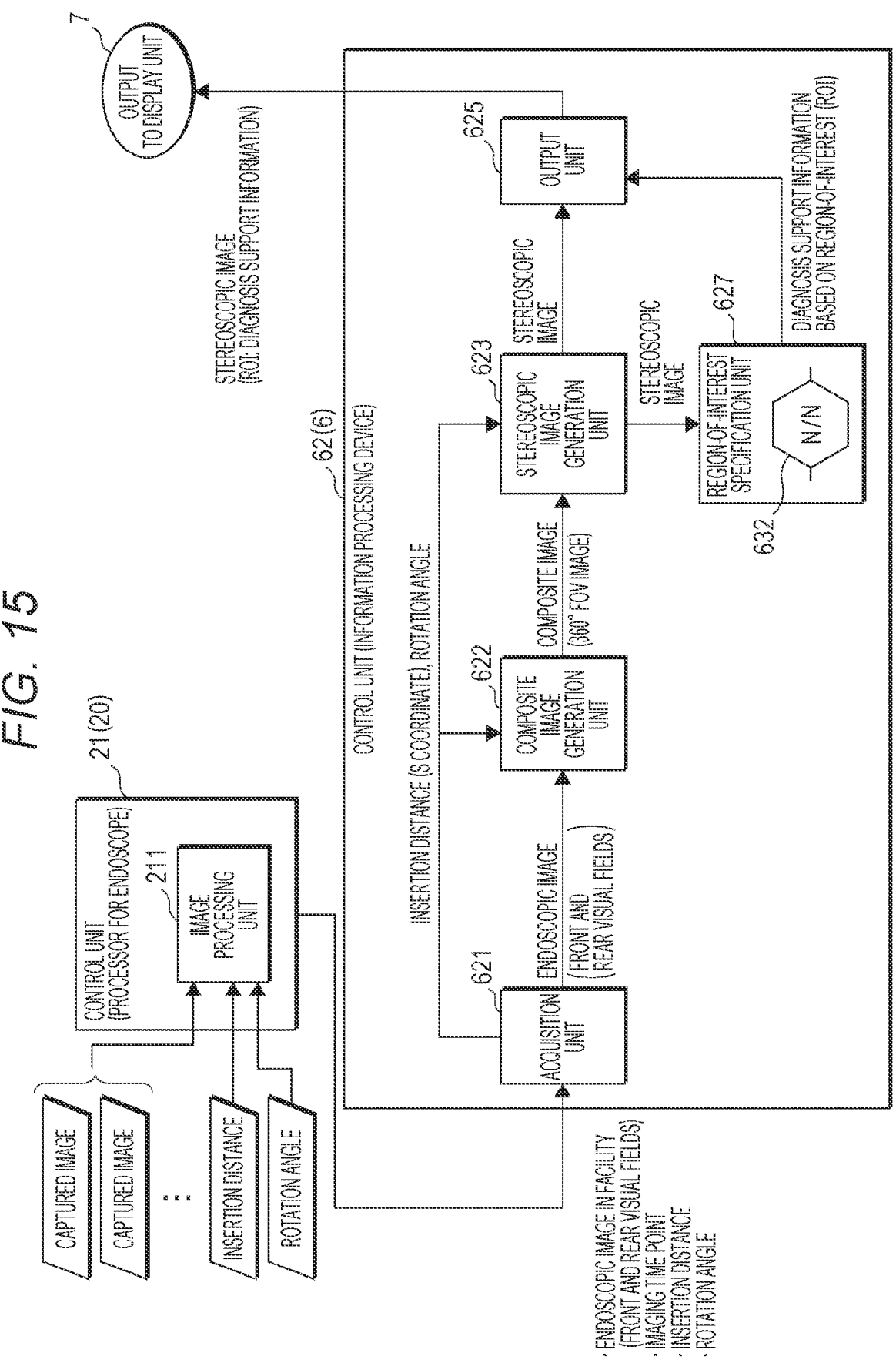
FIG. 15 is a functional block diagram exemplifying functional units included in the control unit of the information processing device according to a fourth embodiment (stereoscopic image).

An endoscope system S according to a fourth embodiment is different from that of the first embodiment in that a stereoscopic image is generated on the basis of composite images. FIG. 15 is a functional block diagram exemplifying functional units included in the control unit 62 of the information processing device 6 according to the fourth embodiment (stereoscopic image). The control unit 21 of the processor 20 for an endoscope (endoscope device 10) executes the program stored in the main storage device 22, thereby functioning as the image processing unit 211. As in the first embodiment, the control unit 62 of the information processing device 6 executes the program stored in the storage unit 63 to function as the acquisition unit 621, the composite image generation unit 622, and the output unit 625, and further function as a stereoscopic image generation unit 626 and a region-of-interest specification unit 627 (region-of-interest learning model 632).

As in the first embodiment, the acquisition unit 621 acquires a plurality of endoscopic images, the S coordinate (insertion distance), and the rotation angle output from the processor 20 for an endoscope. As in the first embodiment, the composite image generation unit 622 generates composite images (360 degree fOV images) having the entire circumference (360 degrees) with respect to the distal end portion 443, including the front and rear visual fields with respect to the advancing direction of the insertion portion 44, on the basis of a plurality of acquired endoscopic images, and outputs the generated Composite images to the stereoscopic image generation unit 626.

Based on the acquired composite images and the insertion distances and rotation angles associated with the composite images, the stereoscopic image generation unit 626 generates a stereoscopic image in which a plurality of endoscopes 40 captured in different visual field directions are arranged for the same observation site in the body of the subject. The stereoscopic image generation unit 626 generates (reconstructs) a stereoscopic image by dividing each of the plurality of composite images at different imaging time points at a predetermined viewing angle according to each viewing direction, performing alignment on each of the divided composite images on the basis of the rotation angles of the endoscope 40, and performing a process of connecting the composite images according to the insertion distances of the endoscope 40.

Figure 16:
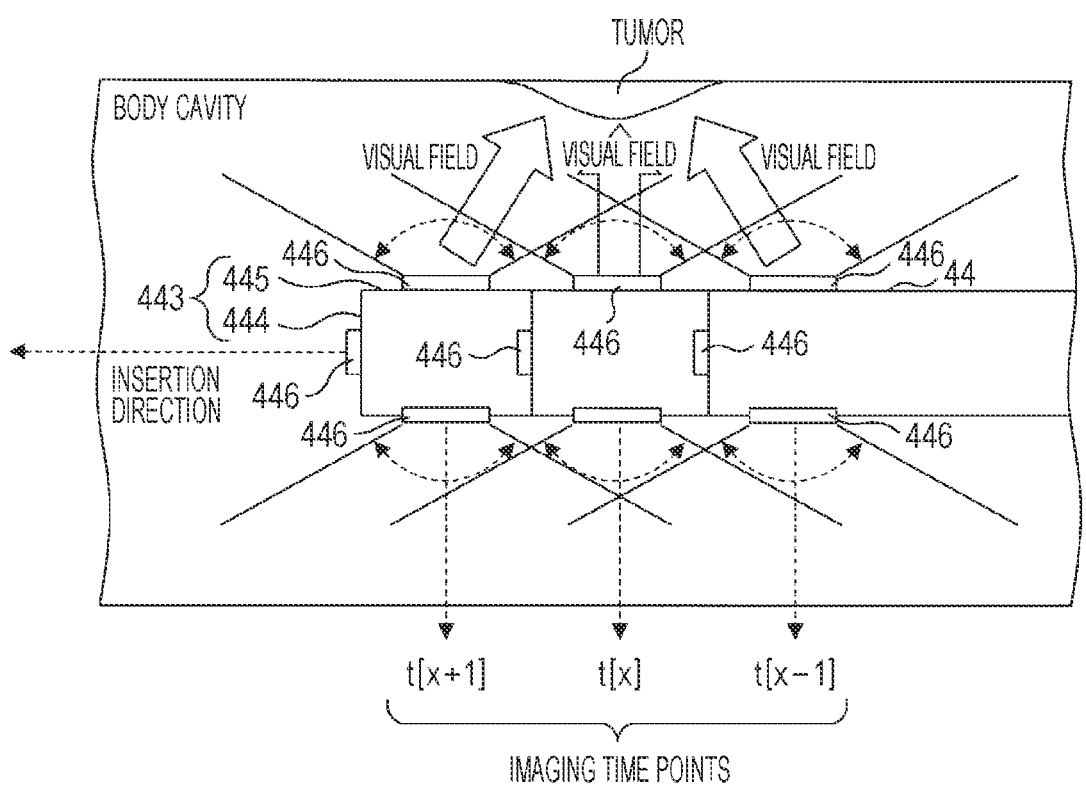
FIG. 16 is an explanatory diagram schematically illustrating image capturing by the imaging units provided at the distal end portion of the insertion portion.

FIG. 16 is an explanatory diagram schematically illustrating image capturing by the imaging units 446 provided at the distal end portion 443 of the insertion portion 44. As illustrated in the present embodiment, the insertion portion 44 of the endoscope 40 is inserted into the body at a predetermined speed (insertion speed), so that it is possible to capture endoscopic images in different viewing directions with respect to the same observation site such as a tumor at a plurality of consecutive imaging time points.

In the illustration in the present embodiment, the imaging units 446 of the peripheral surface 445 capture images of the tumor (observation site) from the front at the imaging time point t[x], captures images of the tumor (observation site) from the left side surface (front visual field) at the imaging time point t[x−1] that is before t[x], and captures images of the tumor (observation site) from the right side surface (rear visual field) at the imaging time point t[x+1] that is after t[x]. In this manner, it is possible to generate a composite image (360 degree fOV image) at each imaging time point on the basis of endoscopic images captured at a plurality of consecutive imaging time points for the same observation site (tumor).

Figure 17:
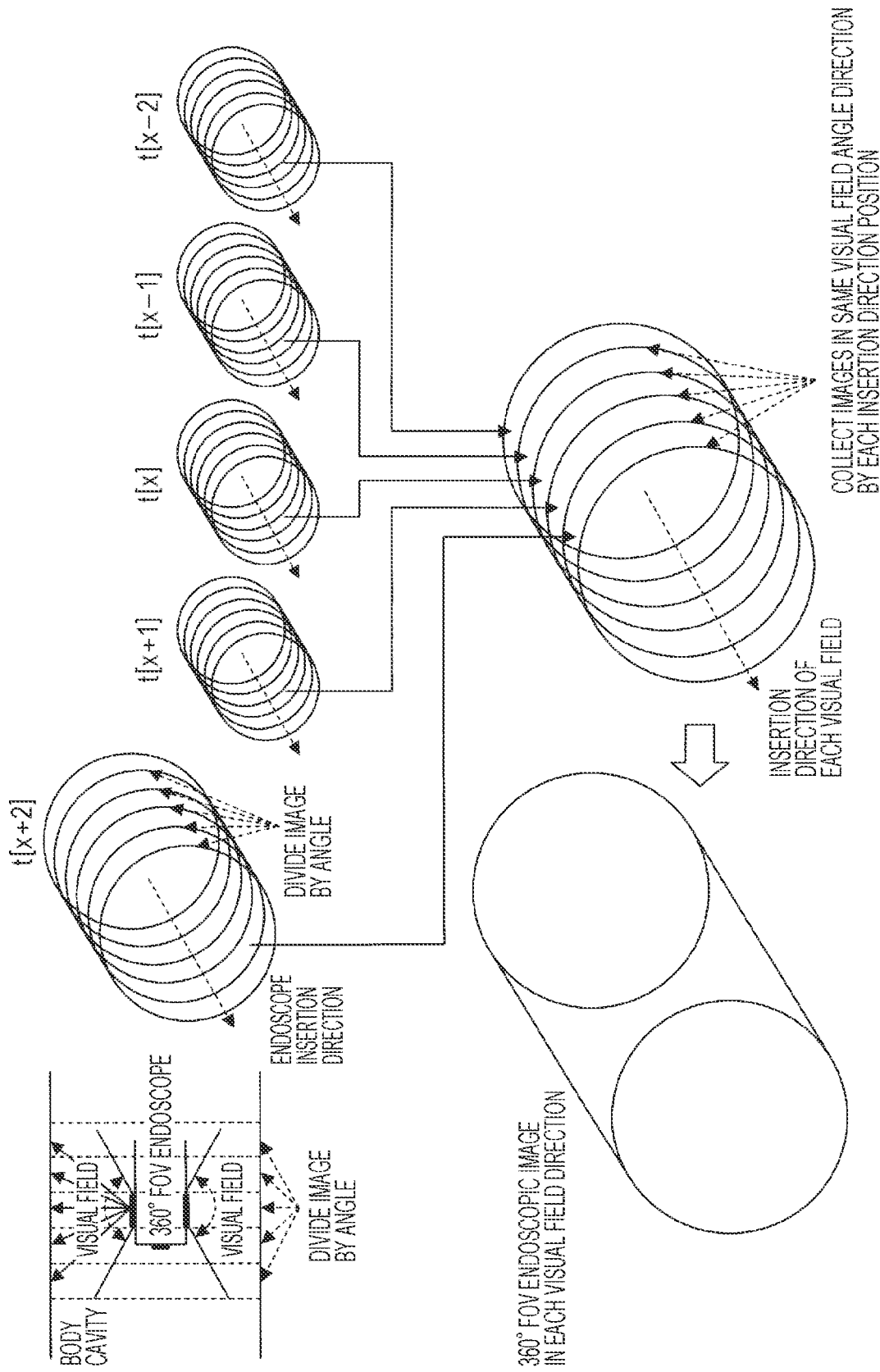
FIG. 17 is an explanatory diagram related to the relationship between the composite images in an entire circumferential direction and a stereoscopic image.

FIG. 17 is an explanatory diagram related to the relationship between the composite images in the entire circumferential direction and the stereoscopic image. Since the composite images (360 degree fOV image) are obtained by combining the endoscopic images captured by the plurality of imaging units 446 provided on the end surface 444 and the peripheral surface 445 of the distal end portion 443 having a tubular shape, the composite images can be indicated by a curved surface coordinate system (cylindrical curved surface coordinate system) formed on the inner wall side of the cylindrical body as illustrated in the present embodiment.

In the cylindrical curved surface coordinate system, the stereoscopic image generation unit 626 divides (slices) the composite image at a predetermined viewing angle, and extracts a divided composite image including a target observation site (tumor) from any composite images which are divided (divided composite images). By performing such division and extraction processing on the composite images at a plurality of consecutive imaging time points, the divided composite images including the target observation site (tumor) are specified. The stereoscopic image generation unit 626 generates a stereoscopic image by aligning the specified divided composite images on the basis of the rotation angles of the distal end portion 443, and further arranging and joining (reconstructing) the divided composite images in the order of imaging time points. By generating the stereoscopic image, it is possible to observe the same observation site (tumor) from different angles.

The stereoscopic image generation unit 626 may extract the divided composite images having the same viewing angle from among any of the composite images which are divided (divided composite images) among the composite images at a plurality of consecutive imaging time points, and connect (reconstruct) the divided composite images having the same viewing angle to generate the stereoscopic image. For example, in a case where the same viewing angle is set to 90 degrees with respect to the insertion direction (axial direction) of the insertion portion 44 with the imaging unit 446 on the peripheral surface 445 as a base point, it is possible to generate a stereoscopic image in which divided composite images captured from the front (upper side) with respect to the observation site are connected. The stereoscopic image generation unit 626 outputs the generated stereoscopic image to the region-of-interest specification unit 627 and the output unit 625.

The lesion region specification unit 624 includes the region-of-interest learning model 632 that outputs diagnosis support information including the presence or absence of a region of interest (ROI) such as a tumor, a lesion candidate, a treatment tool, and a marker when an endoscopic image is input. The region-of-interest specification unit 627 inputs the acquired stereoscopic image to the region-of-interest learning model 632 to determine whether or not a region of interest is included in the endoscopic development view, and outputs diagnosis support information including whether or not a region of interest such as a tumor is included in the stereoscopic image to the output unit 625. Further, the region-of-interest specification unit 627 performs comparison display and comparison information output with the development view by the virtual endoscope of the X-ray CT. Since the stereoscopic image is an image formed by combining a plurality of endoscopic images, it is possible to acquire diagnosis support information including whether or not a region of interest such as a tumor is included in the stereoscopic image by inputting the stereoscopic image to the region-of-interest learning model 632. As in the lesion learning model 631 according to the first embodiment, the region-of-interest learning model 632 includes a neural network learned using training data, such as CNN.

Based on the diagnosis support information regarding the region of interest acquired from the region-of-interest specification unit 627 and the stereoscopic image acquired from the stereoscopic image generation unit 626, the output unit 625 outputs, to the display unit 7, the stereoscopic image on which the diagnosis support information is superimposed, for example, Based on the data output from the output unit 625, the display unit 7 displays the stereoscopic image on which the diagnosis support information is superimposed on the display screen included in the display unit 7.

Figure 18:
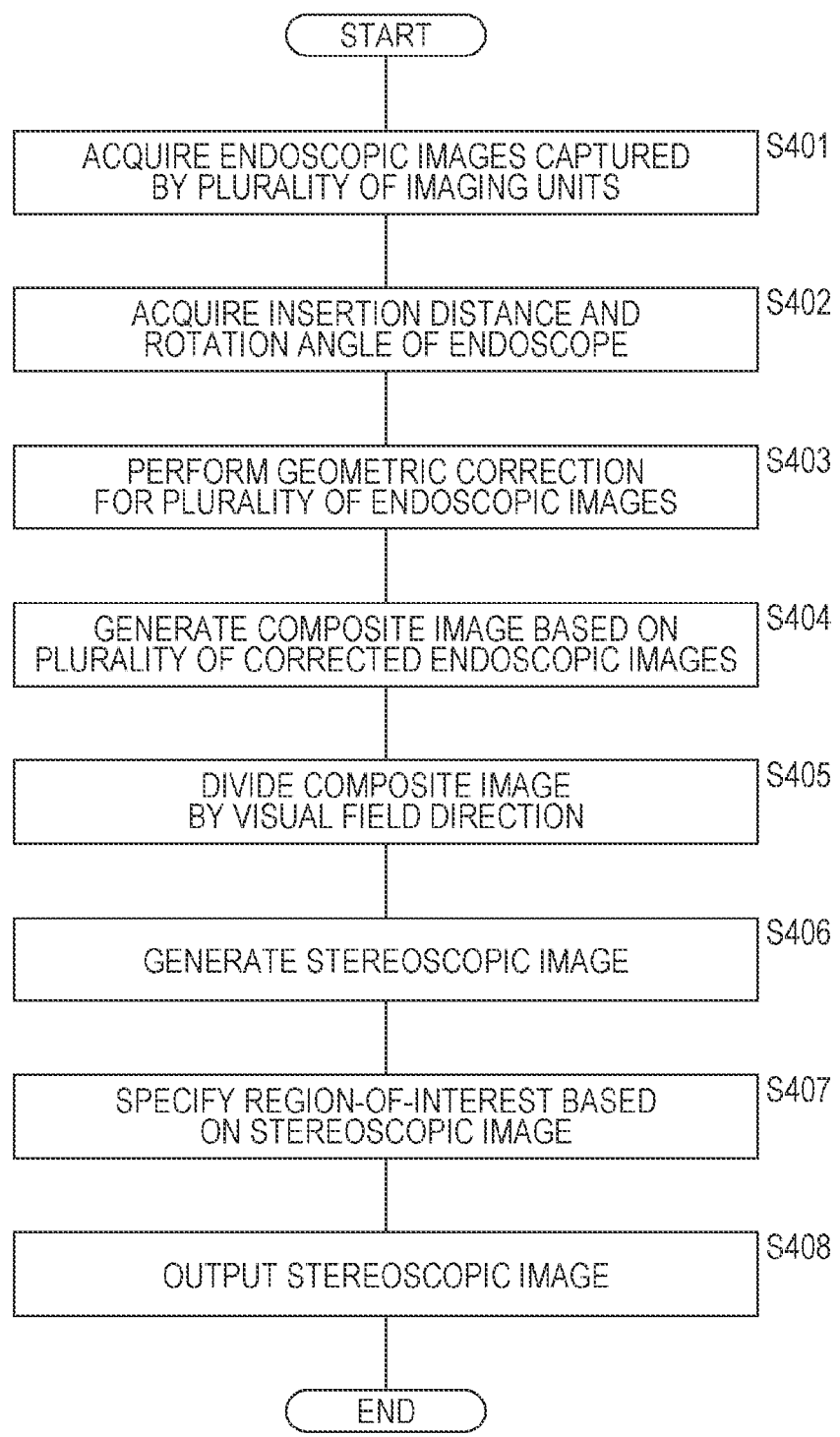
FIG. 18 is a flowchart illustrating an example of a processing procedure performed by a light amount control unit of the endoscope.

FIG. 18 is a flowchart illustrating an example of a processing procedure by the control unit 62. For example, the information processing device 6 starts processing of the flowchart based on a content input from the input unit 8 connected to the device.

The control unit 62 of the information processing device 6 acquires endoscopic images captured by the plurality of imaging units 446 (S401). The control unit 62 of the information processing device 6 acquires the insertion distance and the rotation angle of the endoscope 40 (S402). The control unit 62 of the information processing device 6 performs geometric correction on the plurality of endoscopic images (S403). The control unit 62 of the information processing device 6 generates a composite image on the basis of the plurality of corrected endoscopic images (S404). The control unit 62 of the information processing device 6 performs the processes from S401 to S404 as in the processes from S101 to S104 according to the first embodiment.

The control unit 62 of the information processing device 6 divides the composite image in which the insertion distance and the rotation angle are associated with each other for each visual field direction (S405). As illustrated in the present embodiment, the composite image (360 degree fOV image) can be indicated by a cylindrical curved surface coordinate system formed on the inner wall side of the cylindrical body. In the cylindrical curved surface coordinate system, the control unit 62 of the information processing device 6 divides (slices) the composite image at a predetermined viewing angle, and extracts a divided composite image including a target observation site (tumor) from any of the divided composite images (divided composite images). Alternatively, the control unit 62 of the information processing device 6 may extract divided composite images having the same view angle from among any of the divided composite images (divided composite images).

The control unit 62 of the information processing device 6 generates a stereoscopic image by connecting each of the plurality of divided composite images (S406). By performing such division and extraction processing on the composite images at a plurality of consecutive imaging time points, the divided composite images including the target observation site (tumor) are specified. The control unit 62 of the information processing device 6 generates a stereoscopic image by aligning the plurality of specified divided composite images on the basis of the rotation angles of the distal end portion 443, and further arranging and joining (reconstructing) the divided composite images in the order of imaging time points.

The control unit 62 of the information processing device 6 specifies the region of interest on the basis of the stereoscopic image (S407). The control unit 62 of the information processing device 6 uses, for example, the region-of-interest learning model 632 stored in the storage unit 63 of the own device and inputs a stereoscopic vision image to the region-of-interest learning model 632 to determine whether or not the stereoscopic image includes a region of interest such as a tumor, a lesion candidate, a treatment tool, or a marker, and outputs information regarding the region of interest (diagnosis support information including the presence or absence of the region of interest and the like).

The control unit 62 of the information processing device 6 outputs the stereoscopic image together with the information regarding the region of interest (S408). The control unit 62 of the information processing device 6 outputs, for example, a stereoscopic image on which diagnosis support information is superimposed to the display unit 7 on the basis of the information regarding the region of interest (diagnosis support information) and the stereoscopic image. Based on the output data, the display unit 7 displays, for example, a stereoscopic image on which diagnosis support information is superimposed on a display screen included in the display unit 7.

According to the present embodiment, a plurality of composite images can be generated on the basis of endoscopic images captured at a plurality of time points. The plurality of generated composite images is captured at different time points, and the insertion distance and the rotation angle of the endoscope 40 are different according to the time points. On the other hand, by aligning the respective composite images divided according to the respective visual field directions on the basis of the rotation angle of the endoscope 40, it is possible to absorb the difference in the rotation angle of the endoscope 40 at the time of capturing the composite image and connect the respective divided composite images (divided composite images). Furthermore, by connecting the divided composite images (divided composite images) according to the insertion distance (S coordinate) of the endoscope 40, it is possible to align and connect the divided composite images in the insertion direction of the endoscope 40 on the basis of the order of imaging time points. By generating a stereoscopic image in which a plurality of endoscopes 40 captured in different visual field directions are arranged for the same observation site in the body of the subject on the basis of such a plurality of composite images, three-dimensional confirmation (confirmation in the height direction) and the like can be easily performed, and a stereoscopic image having excellent visibility can be efficiently generated.

According to the present embodiment, when an endoscopic image is input, the stereoscopic image is input to the region-of-interest learning model 632 that outputs diagnosis support information including the presence or absence of a region of interest (ROI) such as a tumor, a lesion candidate, a treatment tool, and a marker, whereby diagnosis support information including whether or not a region of interest such as a tumor is included in the stereoscopic image can be acquired. According to the present embodiment, it is possible to perform endoscopic development view display or stereoscopic image display, perform comparison display and comparison information output with the development view by the virtual endoscope of the X-ray CT.

Fifth Embodiment

Figure 19:
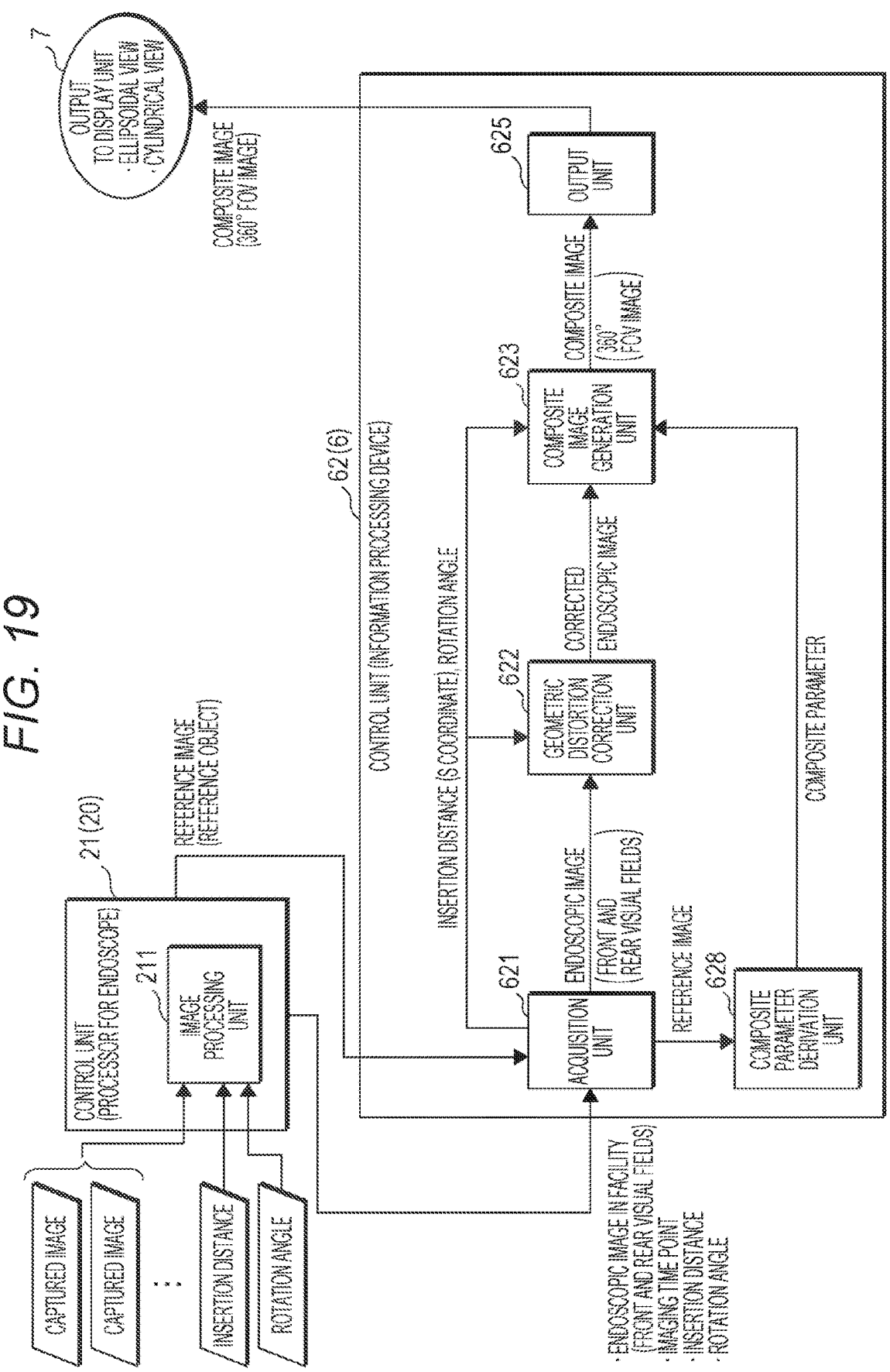
FIG. 19 is a functional block diagram exemplifying functional units included in a control unit of an information processing device according to a fifth embodiment (image composite parameter).

An endoscope system S according to a fifth embodiment is different from that of the first embodiment in that composite images are generated using a composite parameter (image composite parameter) derived based on a reference image. FIG. 19 is a functional block diagram exemplifying functional units included in the control unit 62 of the information processing device 6 according to the fifth embodiment (image composite parameter). The control unit 21 of the processor 20 for an endoscope (endoscope device 10) executes the program stored in the main storage device 22, thereby functioning as the image processing unit 211. As in the first embodiment, the control unit 62 of the information processing device 6 executes the program stored in the storage unit 63 to function as the acquisition unit 621, the composite image generation unit 622, and the output unit 625, and further function as a composite parameter derivation unit 628 and a geometric distortion correction unit 629.

As in the first embodiment, the acquisition unit 621 acquires a plurality of endoscopic images, the S coordinate (insertion distance), and the rotation angle output from the processor 20 for an endoscope. The acquisition unit 621 further acquires a plurality of reference images output from the processor 20 for an endoscope.

The operation unit 43 of the endoscope 40 passes through a mouthpiece or an attachment that also functions as the measurement unit 9 when being inserted into the body, that is, before outputting an endoscopic image obtained by imaging an observation site in the body The mouthpiece and the attachment are provided with a reference object including a predetermined pattern having regularity such as a lattice shape, and each of the imaging units 446 provided at the distal end portion 443 (end surface 444, peripheral surface 445) captures an image of the reference object when passing through the mouthpiece or the like. Each of the captured images (reference images) in which the reference object is captured is output from the processor for the endoscope 40 to the acquisition unit 621 (the control unit 62 of the information processing device 6), and the acquisition unit 621 acquires the reference image. The acquisition unit 621 outputs the acquired reference image to the composite parameter derivation unit 628.

The composite parameter derivation unit 628 derives a composite parameter on the basis of the acquired reference image. The storage unit 63 of the information processing device 6 stores reference object information such as a shape, a dimensional value, and a color of a reference object including a predetermined pattern having regularity. The composite parameter derivation unit 628 compares the reference object included in each of the acquired reference images with the reference object information stored in the storage unit 63, and derives the composite parameter so that the reference object included in the composite image matches the reference object information in the image coordinate system (the coordinate system of the composite image) when the reference images are combined. The composite parameter derivation unit 628 outputs the derived composite parameter to the composite image generation unit 622.

The acquisition unit 621 outputs the acquired plurality of endoscopic images to the geometric distortion correction unit 629. The geometric distortion correction unit 629 performs geometric correction on each of the plurality of acquired endoscopic images to improve extraction accuracy of an overlapping region (overlapping region) in the plurality of endoscopic images and correct the endoscopic images to an image that is easy to combine (an image of a coordinate system that is easy to connect). The geometric correction may be performed, for example, on the basis of image processing algorithms such as spherical correction using curved surface projection (projection transformation) for projecting the acquired endoscopic image onto a continuous curved surface, affine transformation, pseudo-affine transformation, quadratic conformal transformation, and two-dimensional projective transformation. Alternatively, the geometric correction may perform optical simulation on a wide variety of imaged objects on the basis of the specification or optical characteristics of the lens included in the imaging unit 446, generate a dictionary corresponding to the position of the captured image by performing machine learning of the result by artificial intelligence, and perform correction by restoring the dictionary to aberration-free. The geometric distortion correction unit 629 outputs the plurality of endoscopic images subjected to the geometric distortion correction to the composite image generation unit 622.

The composite image generation unit 622 generates a composite image on the basis of the plurality of corrected endoscopic images acquired from the geometric distortion correction unit 629 and the composite parameter acquired from the composite parameter derivation unit 628. By using the composite parameter, the accuracy of the composite image generation can be improved. Since the composite parameter is a parameter derived on the basis of the actual measurement value using the reference object, it is possible to perform composite processing according to the use environment of the imaging unit 446 provided in the distal end portion 443 of the endoscope 40.

Figure 20:
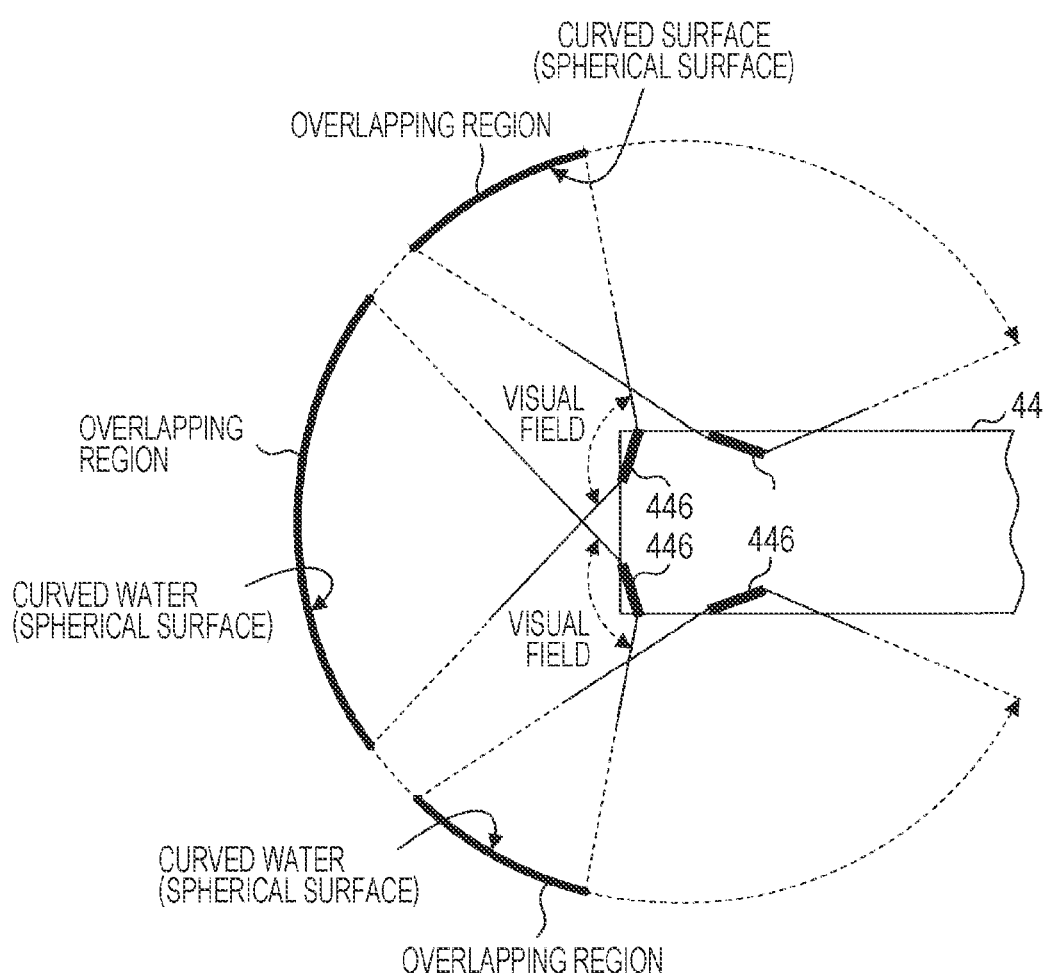
FIG. 20 is an explanatory diagram regarding geometric distortion correction using a curved surface projection method for projecting an endoscopic image onto a continuous curved surface.

FIG. 20 is an explanatory diagram regarding geometric distortion correction using a curved surface projection method for projecting an endoscopic image onto a continuous curved surface. The composite image generation unit 622 generates a composite image by superimposing and aligning overlapping regions (regions where the same observation object is imaged) in a plurality of geometrically corrected endoscopic images. When extracting the overlapping region in the plurality of endoscopic images, the composite image generation unit 622 may extract the overlapping region by performing pattern matching between regions divided in predetermined pixel units in the endoscopic image. By performing the geometric correction, it is possible to efficiently perform spherical correction particularly on a peripheral portion of the endoscopic image. Since the peripheral edge portion becomes a region overlapping with another endoscopic image (overlapping region) and becomes a region to be superimposed at the time of combining, it is possible to correct (convert) the endoscopic image to an endoscopic image which is easy to be superimposed by geometric correction.

Therefore, by combining a plurality of endoscopic images captured by the plurality of imaging units 446 provided in the insertion portion 44 (the end surface 444 and the peripheral surface 445), it is possible to generate a composite image (360 degree fOV image) having the entire circumference (360 degrees) with respect to the distal end portion 443 including the front and rear visual fields in the advancing direction of the insertion portion 44. The composite image generation unit 622 associates the generated composite image with the insertion distance and the rotation angle of the endoscope 40 at the time of capturing a plurality of endoscopic images that are the sources of the composite image. The composite image generation unit 622 may further associate time information regarding a time point (imaging time point) at which a plurality of endoscopic images serving as sources of the composite image is captured with the generated composite image. The composite image generation unit 622 outputs the generated composite image to the output unit 625 as in the first embodiment. The output unit 625 outputs the acquired composite image to the display unit 7 as in the first embodiment.

Figure 21:
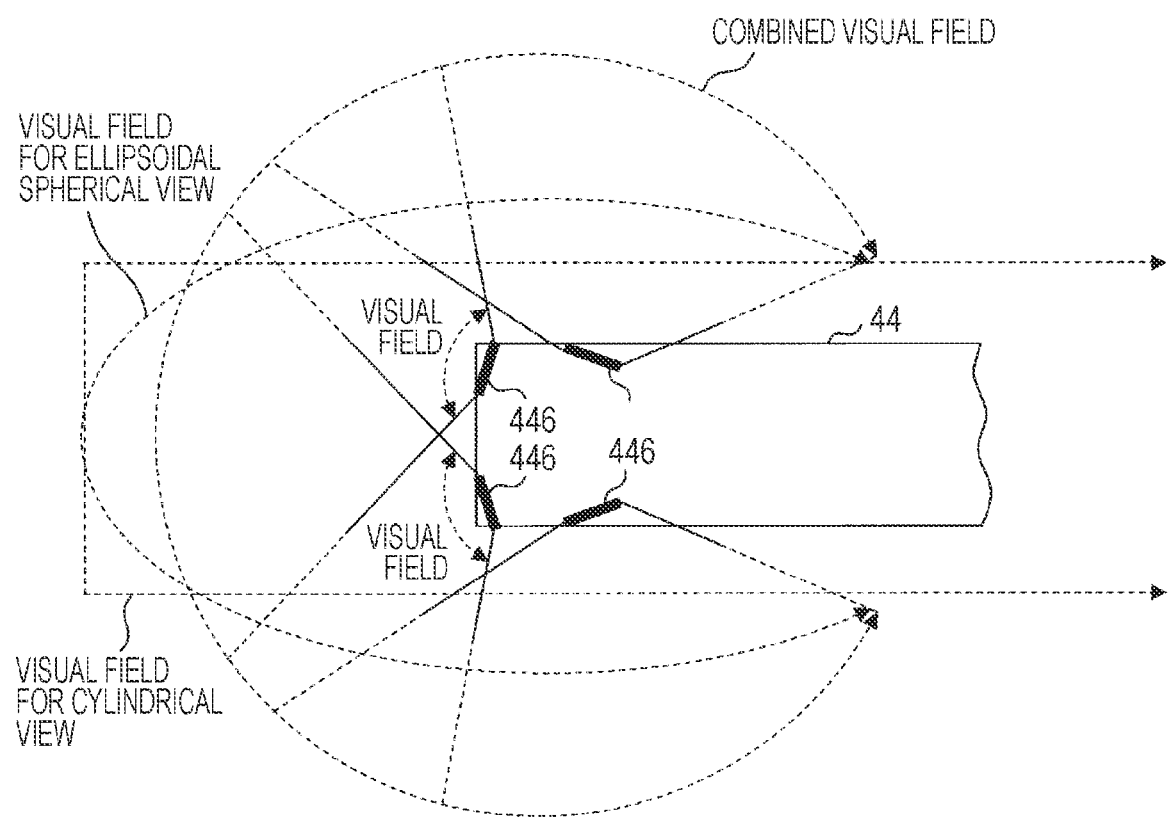
FIG. 21 is an explanatory diagram related to display performed by reprojecting the composite image onto a curved surface (ellipsoidal sphere view, cylindrical view).

FIG. 21 is an explanatory diagram related to display performed by reprojecting the composite image onto a curved surface (ellipsoidal sphere view, cylindrical view). When outputting the composite image to the display unit 7, the output unit 625 may output the composite image to the display unit 7 in a display form (ellipsoidal sphere view, cylindrical view) in which projection transformation is performed so as to obtain a visual field of a coordinate elliptical spherical surface or a cylindrical surface as illustrated in the present embodiment. In this case, the display unit 7 may include a plurality of display screens by a plurality of windows on separate display devices or a single display device, and may divide and display the composite image output in a display form by ellipsoidal sphere view or cylindrical view on the plurality of display screens. In the plurality of display screens, a central portion (front image) of the composite image may be displayed on a display screen positioned at the center, and left and right side portions of the composite image may be displayed on display screens positioned on the left and right, FIG. 22 is a flowchart illustrating an example of a processing procedure by the control unit 62. For example, the information processing device 6 starts processing of the flowchart based on a content input from the input unit 8 connected to the device.

The control unit 62 of the information processing device 6 acquires reference images captured by the plurality of imaging units 446 (S501). When inserted into the body, the operation unit 43 of the endoscope 40 passes through the mouthpiece attached to the oral cavity portion in the case of an upper endoscopy, and the attachment attached to the anal portion in the case of a lower endoscopy, and is inserted into the body. The mouthpiece and the attachment are provided with a reference object having a predetermined pattern having regularity, and each of the imaging units 446 captures an image of the reference object when passing through the mouthpiece or the like. The control unit 62 of the information processing device 6 acquires each of the captured images (reference images) in which the reference object is captured from each of the imaging units 446.

The control unit 62 of the information processing device 6 derives a composite parameter on the basis of the acquired reference image (S502). The storage unit 63 of the information processing device 6 stores reference object information such as a shape, a dimensional value, and a color of a reference object including a predetermined pattern having regularity. The control unit 62 of the information processing device 6 compares the reference object included in each of the acquired reference images with the reference object information stored in the storage unit 63, and derives the composite parameter so that the reference object included in the reference image matches the reference object information in the image coordinate system (the coordinate system of the composite image) when the reference images are combined.

The control unit 62 of the information processing device 6 acquires endoscopic images captured by the plurality of imaging units 446 (8503). The control unit 62 of the information processing device 6 acquires the insertion distance and the rotation angle of the endoscope 40 (S504). The control unit 62 of the information processing device 6 performs geometric correction on the plurality of endoscopic images (S505). The control unit 62 of the information processing device 6 performs processing from S503 to S505 as in the processing from S101 to S103 of the first embodiment.

The control unit 62 of the information processing device 6 generates a composite image using the composite parameter on the basis of the plurality of corrected endoscopic images (S506). The control unit 62 of the information processing device 6 performs as in the processing S104 of the first embodiment, and further generates a composite image by using the composite parameter derived on the basis of the reference image.

The control unit 62 of the information processing device 6 outputs the generated composite image (S507). When outputting the generated composite image, the control unit 62 of the information processing device 6 may output the composite image to the display unit 7 in a display form (ellipsoidal sphere view, cylindrical view) in which projection transformation is performed so as to obtain a visual field of a coordinate elliptical spherical surface or a cylindrical surface. In this case, the display unit 7 may include a plurality of multiple display screens by a plurality of windows on separate display devices or a single display device, and may divide and display the composite image output in a display form by ellipsoidal sphere view or cylindrical view on the plurality of display screens. In the plurality of display screens, a central portion (front image) of the composite image may be displayed on a display screen positioned at the center, and left and right side portions of the composite image may be displayed on display screens positioned on the left and right.

According to the present embodiment, in generating the composite image, the predetermined reference object is imaged by the plurality of imaging units 446 to acquire the reference images including the reference object. Since the composite image is generated using the image composite parameters derived on the basis of the respective reference images captured by the plurality of imaging units 446, the accuracy of the composite processing can be improved. Since the reference image includes the predetermined pattern having regularity, the image composite parameter can be efficiently derived on the basis of the pattern.

According to the present embodiment, since the geometric distortion correction included in the processing of generating the composite image uses the curved surface projection method of projecting the acquired endoscopic image onto a continuous curved surface, it is possible to efficiently perform the superimposition of the overlapping regions (alignment of the overlapping regions) in the endoscopic images particularly when performing the spherical correction on the peripheral edge portion of the endoscopic image and combining the plurality of endoscopic images.

It should be noted that the embodiments disclosed herein are illustrative in all respects and are not restrictive. The technical features described in the embodiments can be combined with each other, and the scope of the present invention is intended to include all modifications and equivalents within the scope of the claims.

REFERENCE SIGNS LIST

S Endoscope system
10 Endoscope device
15 Keyboard
16 Storage rack
20 Processor for an endoscope
21 Control unit
211 Image processing unit
22 Main storage device
23 Auxiliary storage device
24 Communication unit
25 Touch panel
26 Display device I/F
27 Input device I/F
28 Reading unit
31 Endoscope connector
311 Electrical connector
312 Optical connector
33 Light source
34 Pump
35 Water supply tank
36 Air/water supply port
40 Endoscope
43 Operation unit
431 Control button
433 Bending knob
44 Insertion portion
441 Soft portion
442 Bending section
443 Distal end portion
444 End surface
445 Peripheral surface
446 Imaging unit
447 Imaging light source
448 Channel
4481 Wireless communication unit
449 Detection target
45 Bend preventing portion
48 Scope connector
49 Universal cord
50 Display device
6 Information processing device
61 Communication unit
62 Control unit
621 Acquisition unit
622 Composite image generation unit
623 Development view generation unit
624 Lesion region specification unit
625 Output unit
626 Stereoscopic image generation unit
627 Region-of-interest specification unit
628 Composite parameter derivation unit
629 Geometric distortion correction unit
63 Storage unit
630 Recording medium
631 Lesion learning model
632 Region-of-interest learning model
64 Input/output I/F
7 Display unit
8 Input unit
9 Measurement unit
91 Detection unit

The invention claimed is:

1. A non-transitory computer-readable medium containing a program that causes a computer to execute processing comprising:
acquiring endoscopic images obtained by capturing images of a subject by a plurality of imaging units arranged on an end surface and a peripheral surface of a tubular distal end portion provided in an insertion portion of an endoscope;
generating a composite image obtained by combining a plurality of the captured endoscopic images so as to form a view of an entire circumferential direction including a front visual field and a rear visual field with respect to the distal end portion;
acquiring an insertion distance and a rotation angle of the endoscope inserted into a body of the subject at a time point when the endoscopic images are captured;
outputting the composite image in association with the acquired insertion distance and rotation angle of the endoscope;
generating a plurality of the composite images based on the endoscopic images captured at a plurality of time points;
generating an endoscopic development view in which the insertion distance of the endoscope is set to a first axis and the rotation angle of the endoscope is set to a second axis based on the plurality of the composite images, the generating of the endoscopic development view comprising:
  extracting overlapping regions in the plurality of the composite images, and
  generating the endoscope deployment view by superimposing the overlapping regions; and
outputting the generated endoscope development view.

2. The non-transitory computer-readable medium containing a program according to claim 1, wherein
  an angle of an optical axis of the imaging unit arranged on the peripheral surface of the distal end portion with respect to an insertion direction of the insertion portion of the endoscope is larger than 90 degrees.

3. The non-transitory computer-readable medium containing a program according to claim 1, wherein
  in a case where the endoscopic images of the subject are captured by an upper endoscopy, an insertion distance of the endoscope is an insertion distance output from a measurement unit provided in an oral cavity portion of the subject, and
  in a case where the endoscopic images of the subject are captured by a lower endoscopy, the insertion distance of the endoscope is an insertion distance output from a measurement unit provided in an anal portion of the subject.

4. The non-transitory computer-readable medium containing a program according to claim 1, wherein
  in a case where the endoscopic images of the subject are captured by an upper endoscopy, the rotation angle of the endoscope inserted into the body of the subject is an angle with a vertical direction parallel to a body axis of the subject as a rotation axis, and
  in a case where the endoscopic images of the subject are captured by a lower endoscopy, the rotation angle of the endoscope inserted into the body of the subject is an angle with a front-rear direction parallel to a longitudinal direction of a body cavity of the subject as a rotation axis.

5. The non-transitory computer-readable medium containing a program according to claim 1, the processing further comprising:
  specifying a tumor region determined as a tumor in the endoscopic development view using the insertion distance and the rotation angle of the endoscope; and
  outputting the endoscope development view with the specified tumor region being highlighted, or displaying comparison with a development view of a virtual endoscopic image by X-ray CT of a corresponding region.

6. The non-transitory computer-readable medium containing a program according to claim 1, the processing further comprising:
  generating a plurality of the composite images based on the endoscopic images captured at a plurality of time points;
  generating a stereoscopic image in which a plurality of the endoscopic images captured in different visual field directions is arranged for a same observation site in the body of the subject based on the plurality of the composite images; and
  outputting the generated stereoscopic image.

7. The non-transitory computer-readable medium containing a program according to claim 6, wherein
  the processing of generating the stereoscopic image by combining the plurality of the endoscopic images comprises
  dividing each of the plurality of the composite images by each visual field direction, and
  aligning the respective divided composite images based on the rotation angle of the endoscope and joining the images according to the insertion distance of the endoscope.

8. The non-transitory computer-readable medium containing a program according to claim 6, the processing further comprising:
  extracting a region of interest included in the stereoscopic image; and
  outputting diagnosis support information based on the extracted region of interest.

9. An information processing method that causes a computer to execute processing comprising:
  acquiring endoscopic images obtained by capturing images of a subject by a plurality of imaging units arranged on an end surface and a peripheral surface of a tubular distal end portion provided in an insertion portion of an endoscope;
  generating a composite image obtained by combining a plurality of the captured endoscopic images so as to form a view of an entire circumferential direction including a front visual field and a rear visual field with respect to the distal end portion;
  acquiring an insertion distance and a rotation angle of the endoscope inserted into a body of the subject at a time point when the endoscopic images are captured; and
  outputting the composite image in association with the acquired insertion distance and rotation angle of the endoscope;
  generating a plurality of the composite images based on the endoscopic images captured at a plurality of time points;
  generating a stereoscopic image in which a plurality of the endoscopic images captured in different visual field directions is arranged for a same observation site in the body of the subject based on the plurality of the composite images, the generating of the stereoscopic image comprising:
    dividing each of the plurality of the composite images by each visual field direction, and
    aligning the respective divided composite images based on the rotation angle of the endoscope and joining the images according to the insertion distance of the endoscope; and
  outputting the generated stereoscopic image.

10. A non-transitory computer-readable medium containing a program that causes a computer to execute processing comprising:
  acquiring endoscopic images obtained by capturing images of a subject by a plurality of imaging units arranged at a distal end portion provided in an insertion portion of an endoscope;
  generating a composite image obtained by combining a plurality of the captured endoscopic images so as to form a view of an entire circumferential direction including a front visual field and a rear visual field with respect to the distal end portion; and
  outputting the generated composite image, wherein
  the processing of generating the composite image comprises:
    acquiring reference images obtained by capturing images of a predetermined reference object by a plurality of the imaging units,
    deriving an image composite parameter based on the acquired reference images, generating the composite image using the derived image composite parameter, performing geometric distortion correction on the acquired endoscopic images, and combining the plurality of endoscopic images processed in the geometric distortion correction.

11. The non-transitory computer-readable medium containing a program according to claim 10, wherein the reference image includes a predetermined pattern having regularity.

12. The non-transitory computer-readable medium containing a program according to claim 10, wherein the geometric distortion correction is performed using a curved surface projection method of projecting the acquired endoscopic images onto a continuous curved surface.

* * * * *